United States Patent
Hwang et al.

(10) Patent No.: US 7,431,997 B2
(45) Date of Patent: Oct. 7, 2008

(54) PHENYLCARBAZOLE COMPOUNDS AND ORGANIC ELECTROLUMINESCENCE DEVICES USING THE SAME

(75) Inventors: Seok-Hwan Hwang, Suwon-si (KR);
Seok-Jong Lee, Suwon-si (KR);
Young-Kook Kim, Suwon-si (KR);
Seung-Gak Yang, Suwon-si (KR);
Hee-Yeon Kim, Suwon-si (KR);
Chang-Ho Lee, Suwon-si (KR)

(73) Assignee: Samsung SDI Co., Ltd., Gyeonggi-do (KR)

( * ) Notice: Subject to any disclaimer, the term of this patent is extended or adjusted under 35 U.S.C. 154(b) by 198 days.

(21) Appl. No.: 11/181,706

(22) Filed: Jul. 13, 2005

(65) Prior Publication Data

US 2006/0020136 A1    Jan. 26, 2006

(30) Foreign Application Priority Data

Jul. 14, 2004   (KR) ............... 10-2004-0054700

(51) Int. Cl.
*H05B 33/12*   (2006.01)
*C07D 209/82*   (2006.01)

(52) U.S. Cl. .............. 428/690; 428/917; 313/504; 313/506; 548/440; 564/427; 564/434

(58) Field of Classification Search ......... 313/504, 313/506; 428/690, 917; 564/427, 434; 548/440
See application file for complete search history.

(56) References Cited

U.S. PATENT DOCUMENTS

2007/0231503 A1*   10/2007   Hwang et al. ............... 428/1.1

FOREIGN PATENT DOCUMENTS

JP    2005-097460    *   4/2005

* cited by examiner

*Primary Examiner*—Milton I. Cano
*Assistant Examiner*—Camie S Thompson
(74) *Attorney, Agent, or Firm*—Knobbe Martens Olson & Bear LLP

(57) ABSTRACT

A phenylcarbazole compound of formula (1) below is provided,

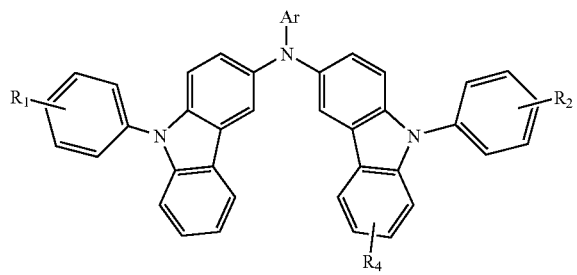

(1)

where each of $R_1$ and $R_2$ is independently a monosubstituted or polysubstituted functional group selected from the group consisting of hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$ and $R_2$ bind and form a saturated or unsaturated cyclic hydrocarbon group, and Ar is a substituted or unsubstituted $C_6$-$C_{30}$ aryl group or a $C_6$-$C_{30}$ heteroaryl group, wherein the substituent $R_4$ is defined herein. Also included is an organic electroluminescence device comprising the above phenylcarbazole compounds.

20 Claims, 3 Drawing Sheets

PHENYLCARBAZOLE COMPOUNDS AND ORGANIC ELECTROLUMINESCENCE DEVICES USING THE SAME

CROSS-REFERENCE TO RELATED PATENT APPLICATIONS

This application claims the benefit of Korean Patent Application No. 10-2004-0054700, filed on Jul. 14, 2004, in the Korean Intellectual Property Office, the disclosure of which is incorporated herein in its entirety by reference.

BACKGROUND OF THE INVENTION

1. Field of the Invention

The present invention relates to an organic luminescent compound, and more particularly, to a new luminescent compound that contains at least two phenylcarbazole derivatives in a molecule and can be used in an emitting layer and/or a hole transporting layer of an organic electroluminescence (EL) device, and organic EL device using the compound.

2. Description of the Related Art

Electroluminescent (EL) devices known as a self-luminous display have the advantages of large viewing angle, high contrast property, and short response time. EL devices can be classified according to the material composing their emitting layer into either inorganic EL devices or organic EL devices. Organic EL devices have the advantages of higher luminance, lower driving voltage, shorter response time, and the ability to display a wider range of colors, over inorganic EL devices.

A general organic EL device includes an anode on the top surface of a substrate, with a hole transporting layer, an emitting layer, an electron transporting layer, and a cathode formed in sequence on the anode, wherein the hole transporting layer, the emitting layer, and the electron transporting layer are thin films made of organic compounds.

Organic EL devices operate according to the following principles. When a voltage is applied across the anode and the cathode, holes injected from the anode migrate via the hole transporting layer into the emitting layer. Electrons injected from the cathode migrate via the electron transporting layer into the emitting layer and combine with the holes therein to generate excitons. When the excitons transit from excited state to base state, fluorescent molecules in the emitting layer emit light to form visible images. Luminescence resulting from a transition from a singlet state ($S_1$) to a base state ($S_0$) is referred to as "fluorescence", and luminescence resulting from a transition from a triplet state ($T_1$) to a base state ($S_0$) is referred to as "phosphorescence". However, only 25% of singlet state excitons can be utilized for fluorescence, and the luminescence efficiency resulting from fluorescence is limited. Meanwhile, 75% of triplet state excitons and 25% of singlet state excitons can be utilized for phosphorescence, theoretically a 100% internal quantum efficiency can be achieved.

An organic EL device with superior green and red luminescence efficiency is disclosed in Nature 750 (Vol. 75, 2000). The organic EL device is manufactured using phosphorescent dyes Ir(ppy)$_3$ and PtOEP, which respectively have heavy elements Ir and Pt with strong spin-orbit binding energy at their center, as dopants and CBP (4,4'-N,N'-dicarbazole-biphenyl) as a host to induce luminescence from phosphorescence in triplet state. However, the lifetime of the organic EL device is short at 150 hours or less, and the organic EL device is not suitable for commercial use. The CBP having a low glass transition temperature of 110° C. or less and being susceptible to crystallization accounts for such a short lifetime of the organic EL device.

SUMMARY OF THE INVENTION

One embodiment provides a new compound that is electrically stable, has the ability to transport charges and a high glass transition temperature, and is not susceptible to crystallization. Another embodiment provides a host material suitable for fluorescent and phosphorescent dopants of any color, i.e., red, green, blue, white, and the like.

Another embodiment provides a high efficiency, low voltage, high luminance, long lifespan organic electroluminescence (EL) device using the compound.

According to one embodiment, there is provided a phenylcarbazole compound of formula (1) below:

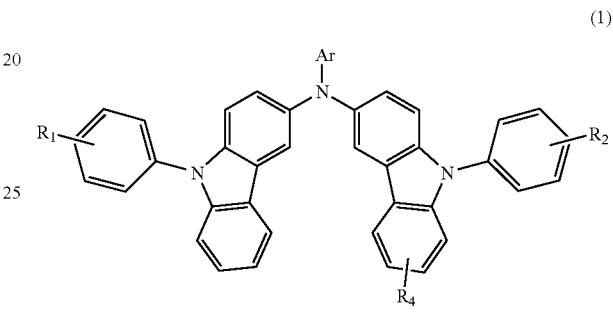

(1)

wherein each of $R_1$ and $R_2$ is independently a monosubstituted or polysubstituted functional group selected from the group consisting of a hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$ and $R_2$ can bind and form a saturated or unsaturated cyclic hydrocarbon group, Ar is a substituted or unsubstituted $C_6$-$C_{30}$ aryl group or a $C_6$-$C_{30}$ heteroaryl group, and $R_4$ is a hydrogen atom or has formula (2) below,

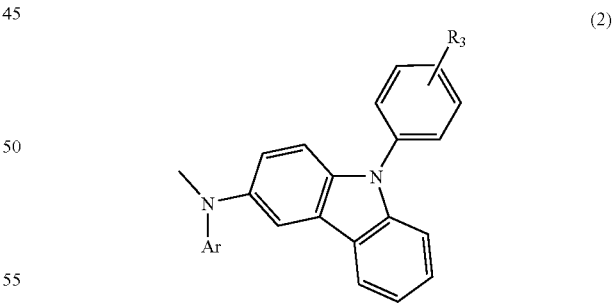

(2)

where $R_3$ is a monosubstituted or polysubstituted functional group selected from the group consisting of a hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, and a substituted or unsubstituted $C_6$-$C_{30}$ condensed polycyclic group; and Ar is a substituted or unsubstituted $C_6$-$C_{30}$ aryl group or a $C_6$-$C_{30}$ heteroaryl group.

The phenylcarbazole compound may be a compound of either formula (3) or (4) below:

(3)

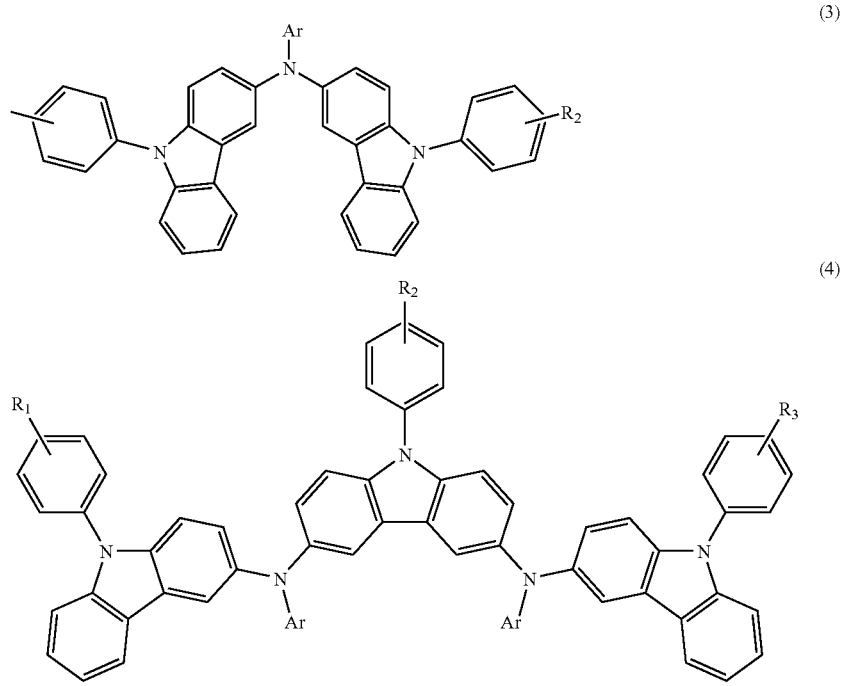

(4)

wherein each of $R_1$, $R_2$, and $R_3$ is independently a monosubstituted or polysubstituted functional group selected from the group consisting of a hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$, $R_2$, and $R_3$ can bind and form a saturated or unsaturated cyclic hydrocarbon group, and Ar is a substituted or unsubstituted $C_6$-$C_{30}$ aryl group or a $C_6$-$C_{30}$ heteroaryl group.

The phenylcarbazole compound may be a compound having formula (5) below:

(5)

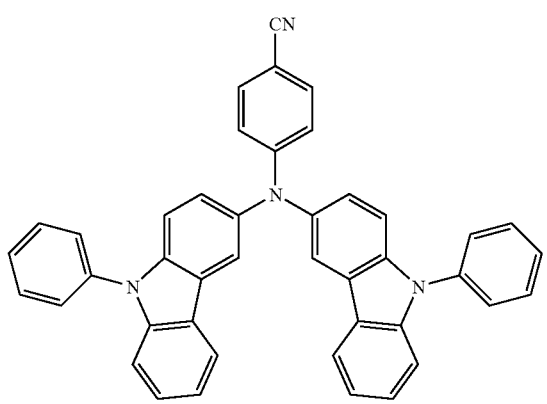

In one embodiment, each of $R_1$ and $R_2$ is independently a monosubstituted or polysubstituted functional group selected from the group consisting of hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$ and $R_2$ can bind and form a saturated or unsaturated cyclic hydrocarbon group, Each of $R_1$, $R_2$, and $R_3$ may be a substituted or unsubstituted $C_6$-$C_{30}$ aryl group independently selected from the group consisting of a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazoyl group, a lower alkyl carbazoyl group, a biphenyl group, a lower alkylbiphenyl group, a lower alkoxybiphenyl group, a thiophenyl group, an indoyl group, a pyrridyl group, and a phenanthrenyl group.

Ar may include one or more 1 to 3 carbon atom substituents and can be selected from the group consisting of a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazoyl group, a lower alkyl carbazoyl group, a biphenyl group, a lower alkylbiphenyl group, a lower alkoxybiphenyl group, a thiophenyl group, an indoyl group, a pyrridyl group, and a phenanthrenyl group.

In a further embodiment, Ar may be selected from the group consisting of a fluorenyl group, a carbazoyl group, a phenyl group, a naphthyl group, a phenanthrenyl group and other aromatic and heteroaromatic groups with 1 to 3 rings.

According to another aspect of the present embodiments, there is provided an organic EL device comprising: a pair of electrodes and an organic layer containing the phenylcarbazole compound of any of formulas 1-5 above.

The organic layer may be an emitting layer or may further include at least one selected from the group consisting of a hole injecting layer, a hole transporting layer, an electron injecting layer, an electron transporting layer, and a hole blocking layer.

The organic layer may be a hole injecting layer or a hole transporting layer.

The emitting layer may contain blue, green, and/or red dopants.

The amount of the blue, green, and red dopants in the emitting layer may be in a range of about 0.1 to about 10 parts by weight based on 100 parts by weight of the phenylcarbazole compound.

BRIEF DESCRIPTION OF THE DRAWINGS

The above and other features and advantages of the present embodiments will become more apparent by describing in detail exemplary embodiments thereof with reference to the attached drawings in which.

DETAILED DESCRIPTION OF THE INVENTION

Figure 1:
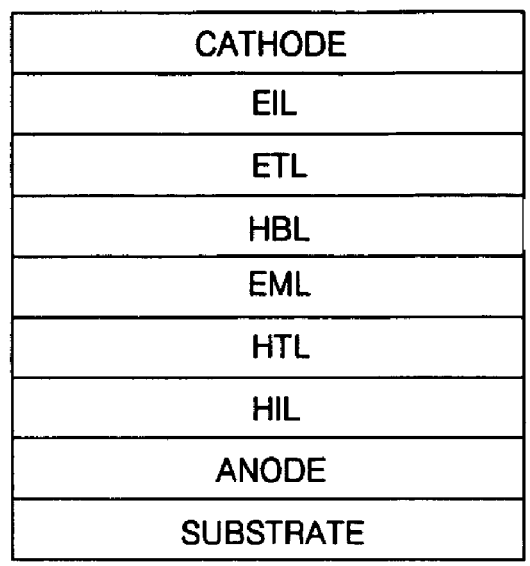
FIG. 1 is a sectional view illustrating a structure of an organic electroluminescence (EL) device according to an embodiment.

The present embodiments will be described in detail with reference to the appended drawings.

A carbazole derivative used as a host material of an emitting layer in an organic electroluminescence (EL) device can be excited to triple state. One embodiment provide a phenylcarbazole compound of formula (1) below:

(1)

where each of $R_1$ and $R_2$ is independently a monosubstituted or polysubstituted functional group selected from the group consisting of a hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$ and $R_2$ bind and can form a saturated or unsaturated cyclic hydrocarbon group, Ar is a substituted or unsubstituted $C_6$-$C_{30}$ aryl group or a $C_6$-$C_{30}$ heteroaryl group, and $R_4$ is hydrogen or has formula (2) below,

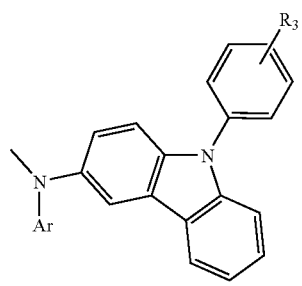

(2)

where $R_3$ is a monosubstituted or polysubstituted functional group selected from the group consisting of a hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, and a substituted or unsubstituted $C_6$-$C_{30}$ condensed polycyclic group; and Ar is the same as defined above.

Examples of a substituted or unsubstituted aryl group for Ar include a phenyl group, an ethylphenyl group, an ethylbiphenyl group, an o-fluorophenyl group, an m-fluorophenyl group, a p-fluorophenyl group, a dichlorophenyl group, a dicyanophenyl group, a trifluoromethoxyphenyl group, an o-tolyl group, an m-tolyl group, and a p-tolyl group, an o-cumenyl group, an m-cumenyl group and a p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, a indenyl group, a naphthyl group, a methylnaphthyl group, an anthracenyl group, an azulenyl group, a heptalenyl group, an acenaphthylenyl group, a fluorenyl group, an anthraquinoyl group, a methylanthryl group, a phenanthryl group, a triphenylene group, a pyrenyl group, a chrysenyl group, an ethyl chrysenyl group, a picenyl group, a perylenyl group, a chloroperylenyl group, a pentaphenyl group, a pentacenyl group, a tetrapenylenyl group, a hexaphenyl group, a hexacenyl group, a rubicenyl group, a coronenyl group, a trinaphthylenyl group, a heptaphenyl group, a heptacenyl group, a phenanthrenyl group, a ovalenyl group, a carbazoyl group, and the like. Preferred examples of the aryl group include phenyl, lower alkylphenyl, lower alkoxyphenyl, cyanophenyl, phenoxyphenyl, halophenyl, naphthyl, lower alkylnaphthyl, lower alkoxynaphthyl, cyanonaphthyl, halonaphthyl, fluorenyl, carbazoyl, lower alkyl carbazoly, biphenyl, lower alkylbiphenyl, lower alkoxybiphenyl, thiophenyl, indoyl, pyrridyl group, and the like. The lower alkyl and lower alkoxy groups include 1 to 5 carbon atoms and the oxygen atom can be anywhere along the chain as an ether function or a hydroxyl function. An aryl group selected from among fluorenyl, carbazoyl, phenyl, naphthyl, and phenanthrenyl, which have 1 to 3 rings, or such an aryl group with one to three or more, preferably, one, $C_1$-$C_3$ lower alkyl, $C_1$-$C_3$ lower alkoxy, cyano, phenoxy, phenyl, or halogen substitutes in aromatic rings constitutes yet another group of examples.

In the above formulas, the term "$C_1$ to $C_{30}$ substituted or unsubstituted alkyl group" means a branched or linear alkyl group optionally substituted with one or more groups selected from the group consisting of hydroxy, carboxy, amino, halogen, amide, nitro, cyano alkoxy and $C_1$ to $C_{30}$ substituted or unsubstituted alkyl group.

In the above formulas, the term "$C_6$ to $C_{30}$ substituted or unsubstituted aryl group" means a phenyl group, substituted or unsubstituted with one or more groups selected from hydroxy, carboxy, amino, halogen, amide, nitro, cyano, and alkoxy, wherein the aryl group can additionally be substituted with a $C_1$-$C_6$ branched or straight chain alkyl or $C_1$ to $C_6$ straight or branched chain alkoxy group; a mono or polycyclic aromatic system bonded to a branched or linear chain $C_1$-$C_{24}$ alkyl group selected so that the total number of carbon atoms of the group does not exceed 30, which alkyl group is in turn bound to the core molecule, all of which can be substituted by one or more groups selected from the group consisting of hydroxy, carboxy, amino, halogen, amide, nitro, cyano and alkoxy.

In the above formulas, the term "substituted or unsubstituted $C_4$ to $C_{30}$ heterocyclic" means a mono or bicyclic saturated, unsaturated or aromatic heterocyclic ring such as azetidine, pyrrolidine, furyl, thienyl, tetrazolyl, pyrrolyl, pyrazolyl, imidazolyl, oxazolyl, thiazolyl, pyridinyl, and triazinyl. Examples of non-aromatic heterocyclic group include pyrrolidinyl, thiazolidinyl, oxazolidinyl, imidazolidinyl, thiazolinyl, oxazolinyl, imidazolinyl, piperidinyl, piperadinyl, morpholinyl, thiomorpholinyl, oxadiazolyl, oxadinyl and dioxanyl which contain 1-4 heteroatoms selected from the group consisting of oxygen, nitrogen, phosphorus or sulfur or such a ring attached to a straight or branched $C_1$-$C_{26}$ alkyl chain selected so that the total number of carbon atoms in the group does not exceed 30, all of which may be substituted by hydroxy, carboxy, amino, halogen, amide, nitro, and cyano, wherein further the heterocyclic ring may additionally be substituted with one or more of a $C_1$ to $C_6$ straight or branched alkyl or alkoxy chains.

In the above formulas, the term "$C_6$ to $C_{30}$ heteroaryl" means substituted or unsubstituted groups such as methylene pyrrole, methylene isoxazole, methylene 1,2,5-oxadiazole, pyridine, pyrimidine, pyrazine, methylene furan, 1,4-oxazine, azepine, indole, cinnoline, quinazoline, napthyridine, acridine, and the like, or one of such heteroaromatic rings attached to a $C_1$ to $C_{25}$ straight or branched chain alkyl group selected so that the total number of carbon atoms of the group does not exceed 30, wherein the substituents are one or more groups selected from hydroxy, carboxy, amino, halogen, amide, nitro, cyano, $C_1$ to $C_6$ alkyl or alkoxy on the rings; wherein the heteroatom of the heteroaryl group is one or more oxygen, sulfur, phosphorus or nitrogen atoms. In the above formulas, the term "$C_6$ to $C_{30}$ condensed polycyclic group" means moieties containing one or more 4, 5, 6, 7 and 8 membered fused carbocyclic rings such as phenyl, napthyl, anthracenyl, phenanthrenyl, phenalenyl, fluorenyl, pentalenyl, indenyl, napthylenyl, azulenyl, heptaleny; biphenylenyl, as-indacenyl, s-indacenyl, acenaphthylenyl, fluorenyl, phenalenyl, phenanthrenyl, anthracenyl, fluoranthenyl, acephenanthrylenyl, aceanthrylenyl, triphenylenyl, pyrenyl, chrysenyl, naphthacenyl, pleiadenyl, picenyl, perylenyl, pentaphenyl, pentacenyl, tetraphenylenyl, hexaphenyl, hexacenyl, rubicenyl, coronenyl, trinaphthylenyl, heptaphenyl, heptacenyl and the like. In the above formulas, the term "halo" or "Halogen" means fluoro, chloro, bromo, or iodo.

The new compounds according to one embodiment has a high glass transition temperature or a high melting point because it contains a rigid carbazol group. Accordingly, the new compound has improved resistance to Joule heat generated in or between organic layers or between an organic layer and a metal electrode and resistance under high temperature environment. Therefore, when the compound is used as a material for a hole transporting layer, a luminescent material, or a host material for an emitting layer in an organic EL device, the luminance and the duration of luminescence of the EL device are improved. These effects are considerable because the compound includes at least two rigid carbazol groups in its molecular structure. The phosphorescent dopant is typically doped into a conventional host, such as Alq3 or CBP, allowing singlet excitons to transfer from the host to the dopant by Föster or Dexter transfer. The singlets subsequently intersystem cross to the phosphorescent triplet state. Additionally, host triplet excitons reach phosphorescent dopant by Dexter transfer or by direct charge carrier trapping. As described in "Organic Luminescent Materials" (VCH, 1988), carbazole groups definitely increase the probability of singlet to triplet conversion allowing for extremely high external quantum efficiency of the EL device. Therefore, a high luminance, high efficiency organic EL device can be manufactured using the carbazol group. The compounds represented by formula (1) can be used as luminescent materials and hole transporting materials. Non-limiting representative structos of the new compounds according to the present embodiment are each separately illustrated below.

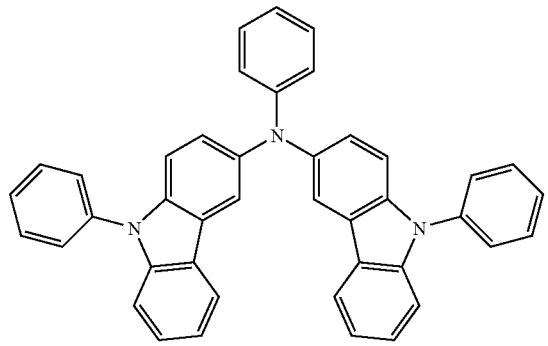

1

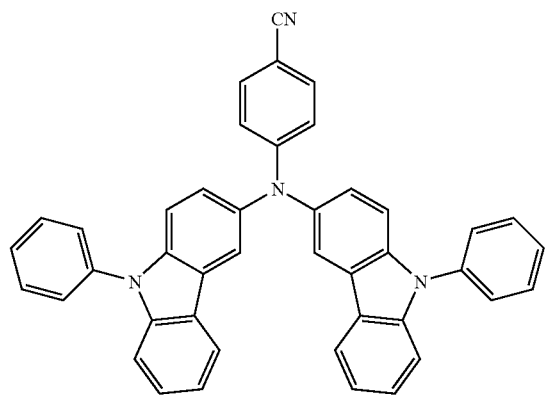

2

3
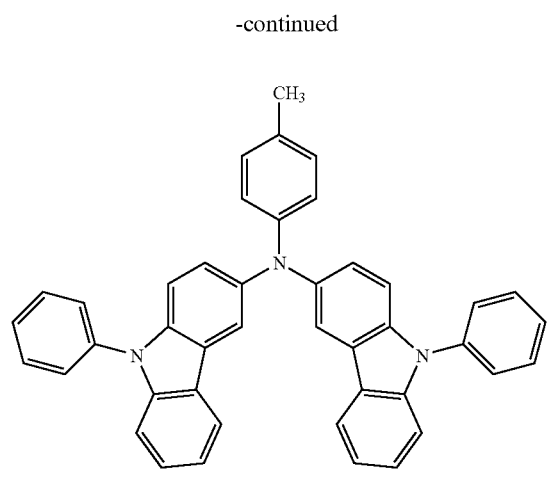
4
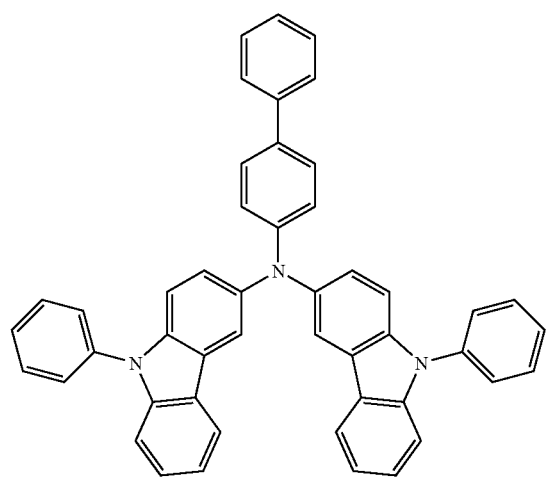
5
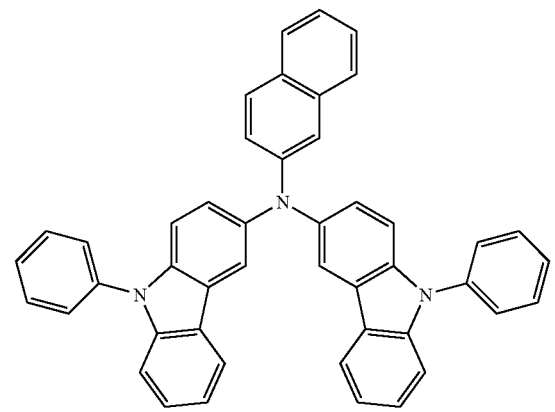
6
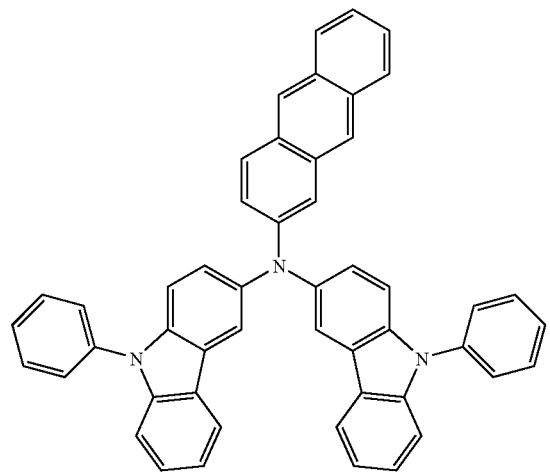
7
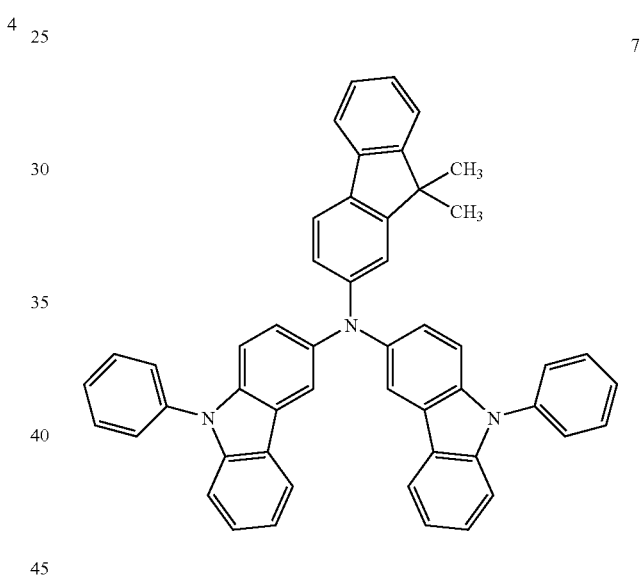
8
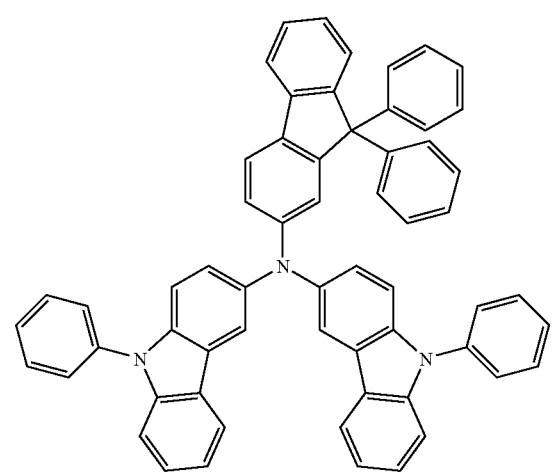

9
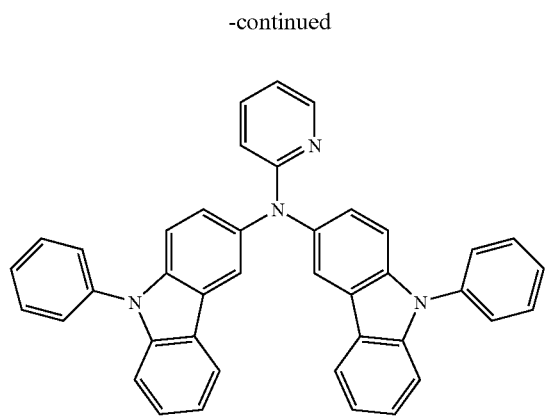
10
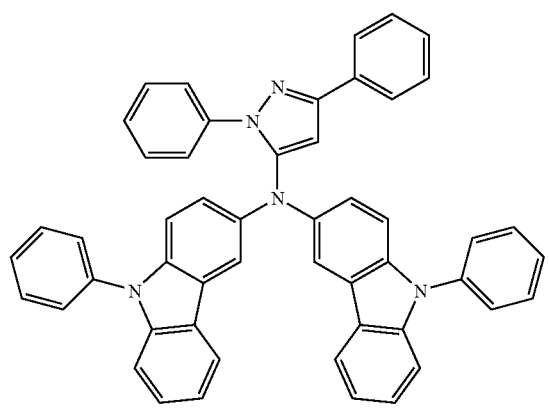
11
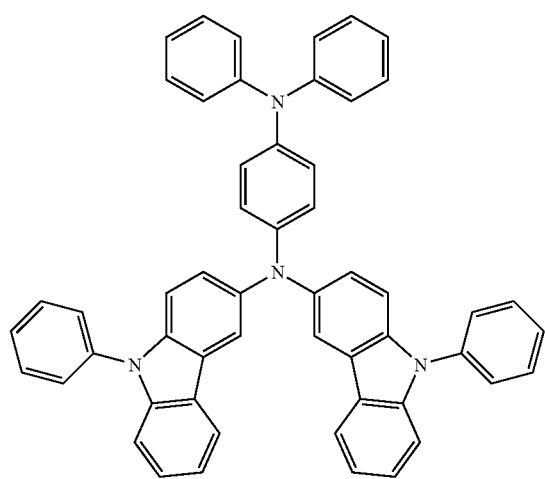
12
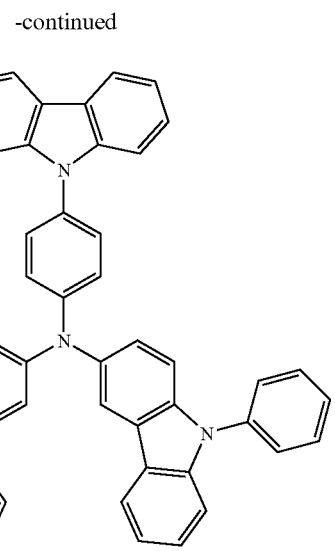
13
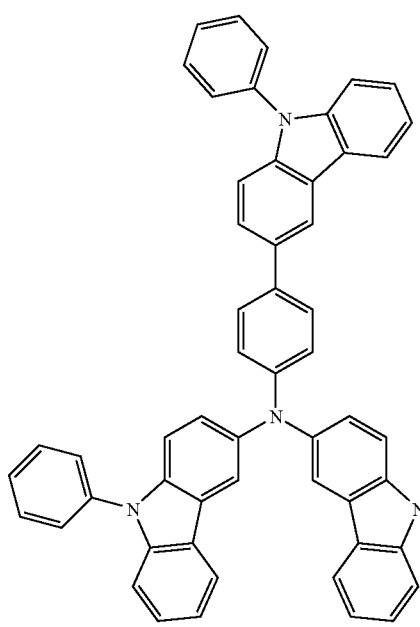
14

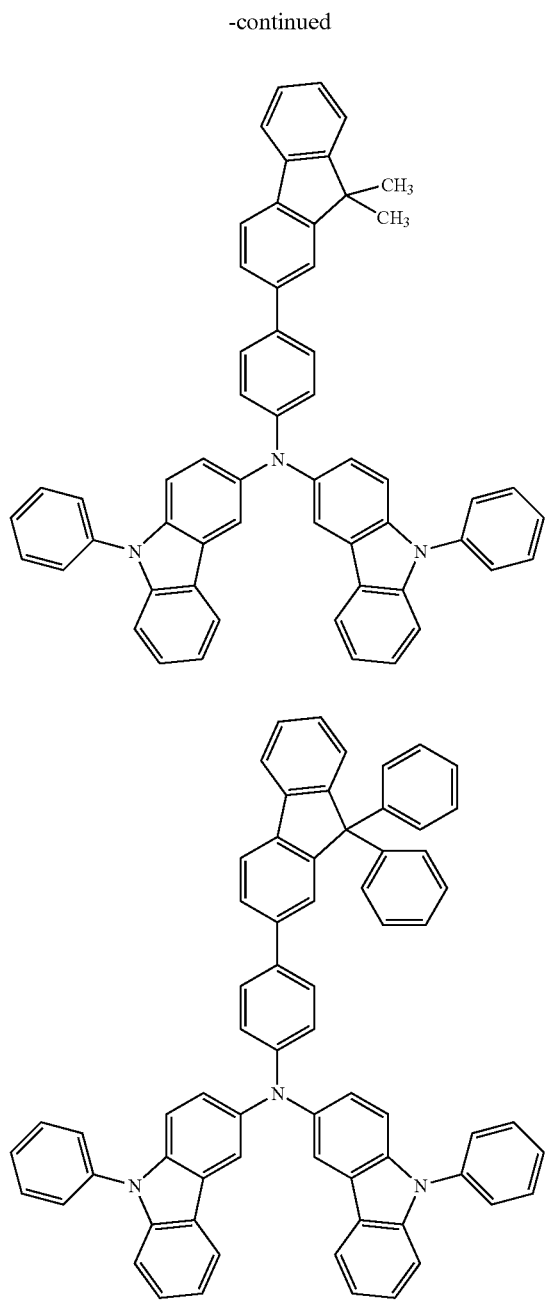
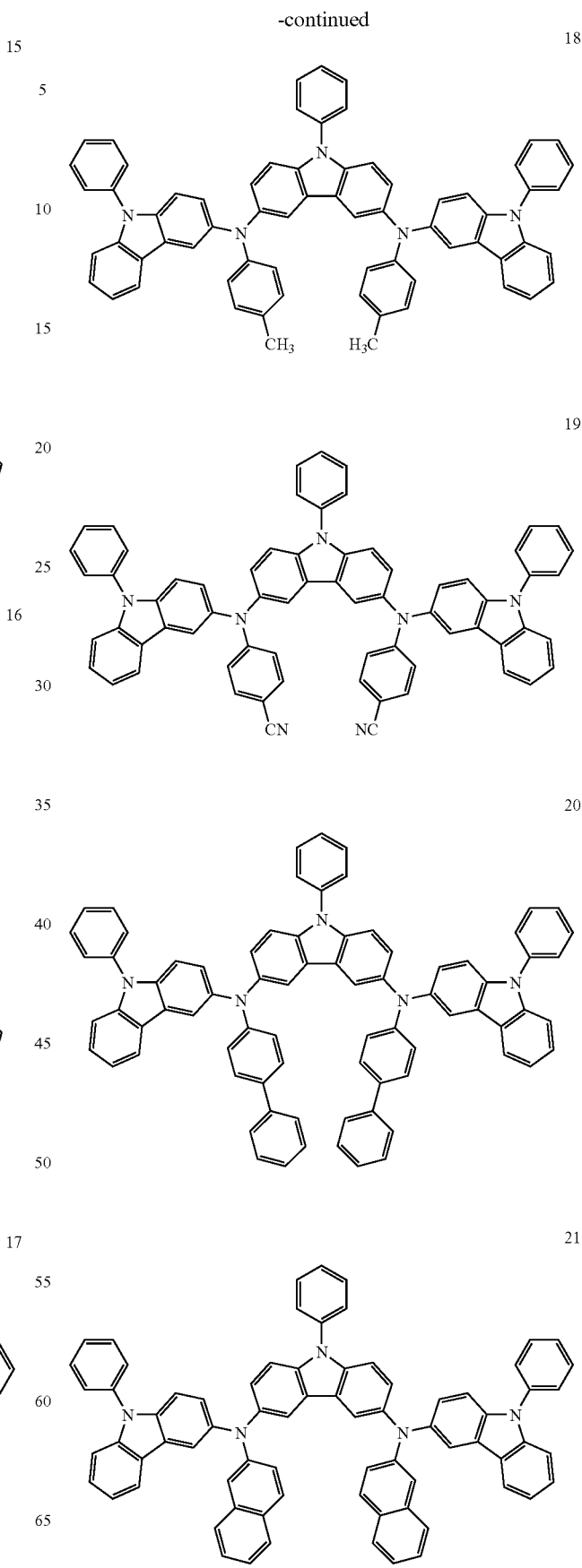

-continued

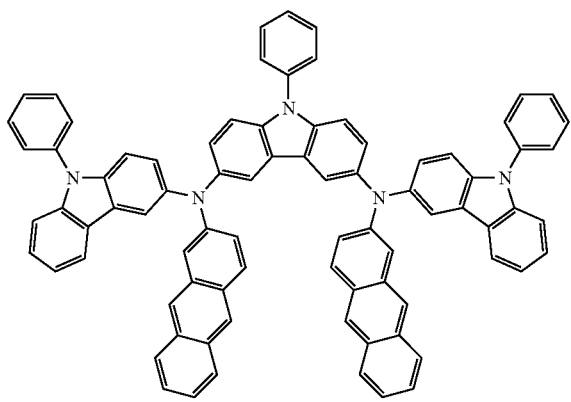

22

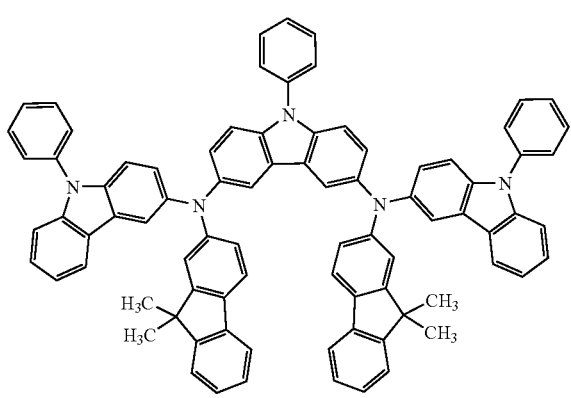

23

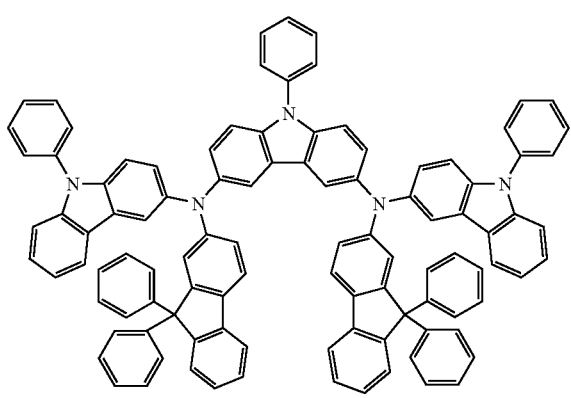

24

In another aspect, there is provided an organic EL device including a pair of electrodes and a mono-layered or multi-layered organic layer including an emitting layer between the electrodes, wherein the organic layer contains a phenylcarbazole compound of any of formulas 1-5.

FIG. 1 is a sectional view illustrating a structure of an organic EL device according to one embodiment. Initially, an anode is formed on a surface of a substrate using a material having a high work function by deposition or sputtering. A substrate commonly used in organic EL devices is used for the substrate. A glass substrate or a transparent plastic substrate which is mechanically strong, thermally stable, transparent, easy to handle, and waterproof, and has a flat surface may be used. Examples of the material for the anode include ITO, IZO, $SnO_2$, ZnO, and the like, which are transparent and have superior conductivity.

Next, a hole injecting layer (HIL) is formed on the anode using vacuum deposition, casting, an LB method, and the like. However, the use of vacuum deposition is preferred to form a uniform thin layer and to prevent generation of pin holes. When forming the HIL using vacuum deposition, the deposition conditions may vary according to the compound used as a material for the HIL and the intended structure and thermal characteristics of the HIL, and the like. In general, when forming the HIL using vacuum deposition, the deposition temperature may be in a range of from about 50 to about 500° C., the level of vacuum may be in a range of from about $10^{-8}$ torr to about $10^{-3}$ torr, the deposition rate may be in a range of about 0.01 to about 100 Å/sec, and the thickness of the HIL may be in a range of about 10 Å to about 5 µm. Any material can be used for the HIL without limitation. For example, phthalocyanine compounds, such as copper phthalocyanine disclosed in U.S. Pat. No. 4,356,429, or starburst amine derivatives, such as TCTA, m-MTDATA, m-MTDAPB, etc., disclosed in "Advanced Materials", Vol. 6, p. 677 (1994), can be used as materials for the HIL.

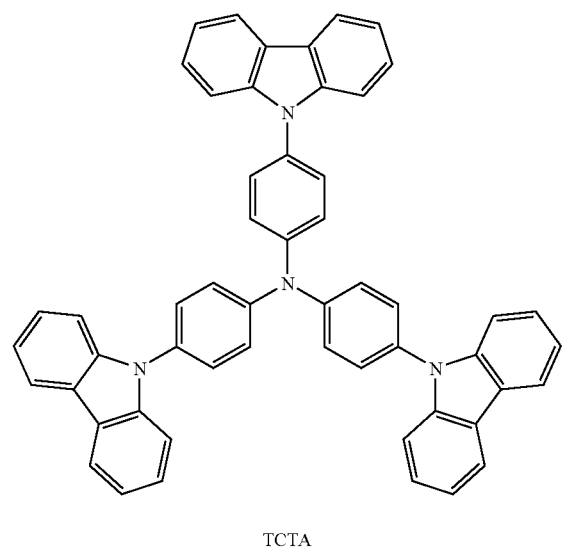

TCTA

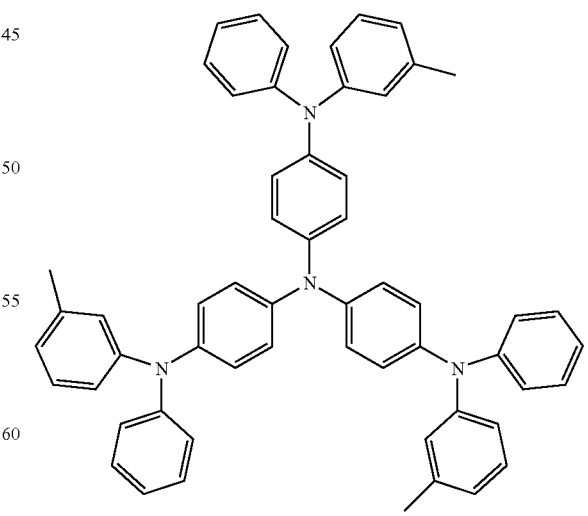

m-MTDATA

Next, a hole transporting layer (HTL) is formed on the HIL using vacuum deposition, spin coating, casting, an LB method, and the like. However, the use of vacuum deposition is preferred to form a uniform thin layer and to prevent generation of pin holes. When forming the HTL using vacuum deposition, the deposition conditions vary according to the compound used as a material for the HTL. However, the HTL is formed under almost the same conditions as applied to form the HIL. Any material can be used for the HTL without limitation. An organic luminescent compound according to one embodiment or a material commonly used for the HTL can be used as a material for the HTL. For example, carbazole derivatives, such as N-phenylcarbazole, polyvinylcarbazole, and the like, amine derivatives having aromatic condensed rings, such as N,N'-bis(3-methylphenyl)-N,N'-diphenyl -[1,1-biphenyl]-4,4'-diamine (TPD), N,N'-di(naphthalene-1-yl)-N,N'-diphenyl benzydine (α-NPD), and the like can be used.

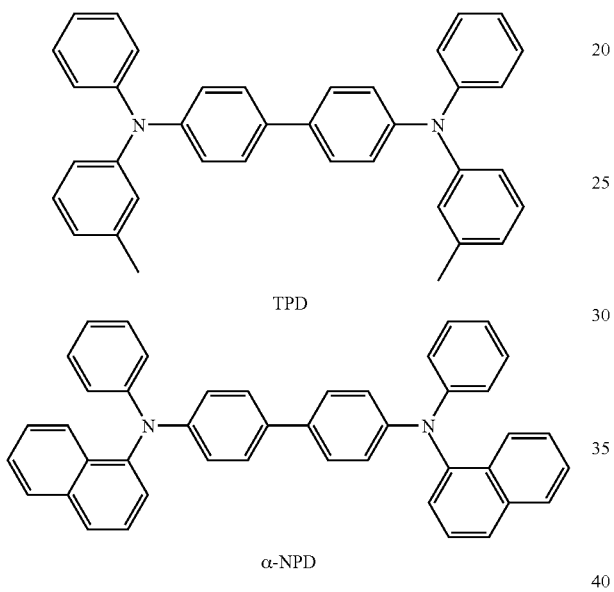

Next, an emitting layer (EML) is formed on the HTL using vacuum deposition, spin coating, casting, an LB method, and the like. However, the use of vacuum deposition is preferred to form a uniform thin layer and to prevent generation of pin holes. When forming the EML using vacuum deposition, the deposition conditions vary according to the compound used as a material for the EML. Any material can be used for the EML without limitation. A compound of formula (1) according to one embodiment, can be used alone or in combination with other materials as a phosphorescent host material suitable for blue, green, and/or red phosphorescent dopants in the EML. A concentration of the compound of formula (1) according to the present embodiment may be in a range of about 90 to about 99.9 parts by weight based on the amount of phosphorescent dopants. When the compound of formula (1) is used as a luminescent host, common fluorescent dopants, such as IDE102, IDE105 (available from Idemitsu (Tokyo, Japan)), and the like and common phosphorescent dopants, such as a green phosphorescent dopant, Ir(ppy)$_3$, a blue phosphorescent dopant, F$_2$Irpic, a red phosphorescent dopant, RD 61 (available from Universal Display Corporation, Ewing, N.J.), and the like can be doped by vacuum deposition. A concentration of the dopants is not limited but may be in a range of about 0.01 to about 15% by weight of the host. The compound of formula (1) can be used as a fluorescent host material for blue, green, and red fluorescent dopants in the EML. A concentration of the fluorescent dopant may be in a range of about 90 to 99.9 parts by weight based on the amount of the blue, green, and red fluorescent dopants in the EML.

When the compound of formula (1) is used together with a phosphorescent dopant in the EML, a hole blocking layer (HBL) may be additionally formed using vacuum deposition or spin coating to prevent diffusion of triplet excitons or holes into the ETL. Any common hole blocking material can be used for the HBL. For example, oxadiazole derivatives, triazole derivatives, phenanthroline derivatives, or hole blocking materials disclosed in Japanese Laid-open Patent Publication No. 11-329734(A1) can be used. However, Balq, TPBI, BCP, and the like, are among the preferred compounds.

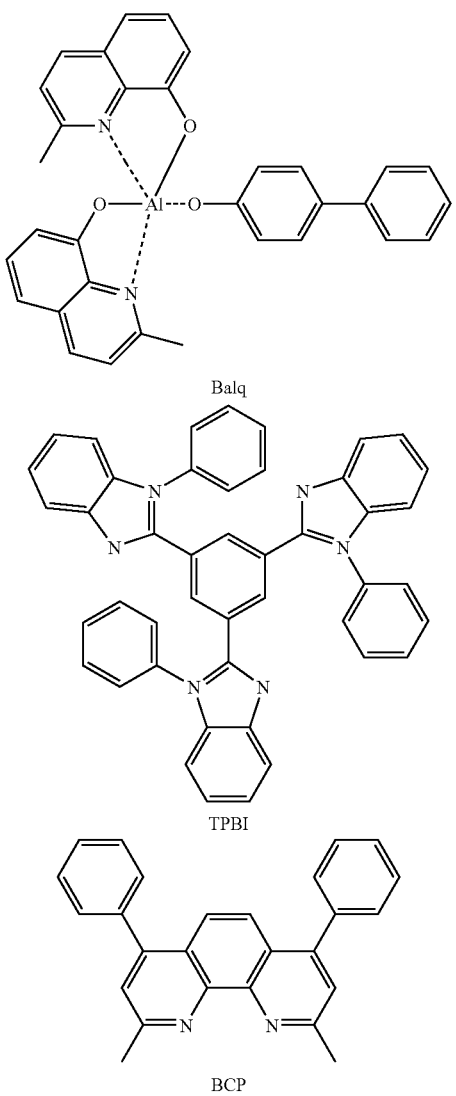

Next, an electron transporting layer (ETL) is formed using vacuum deposition, spin coating, casting, and the like. However, vacuum deposition is preferred. Any materials that can stably transport electrons injected through an electron injection electrode (cathode), for example, quinoline derivatives, preferably, tris(8-quinolinolate)aluminum (Alq3) can be used.

An electron injecting layer (EIL), which makes it easier to inject electrons through the cathode, may be formed on the ETL. Any material can be used for the EIL without limitation.

Examples of a material for the EIL include LiF, NaCl, CsF, $Li_2O$, BaO, and the like. The deposition conditions for the HBL, ETL, and EIL vary according to the compound used for each of the layers. However, the HBL, ETL, and EIL may be formed under substantially the same conditions as for the HIL.

Finally, a metal is deposited on the EIL using vacuum deposition, sputtering, and the like, to form a cathode. A metal having a low work function, an alloy thereof, an electrically conductive compound, and/or a mixture of the forgoing materials can be used for the cathode. In particular, examples of the metal for the cathode include Li, Mg, Al, Al—Li, Ca, Mg—In, Mg—Ag, and the like. A transmissive cathode formed using ITO, IZO, and the like, can be used to manufacture a front luminescence device.

An organic EL device according to one embodiment may have various structures in addition to the structure including the anode, the HIL, the HTL, the EML, the ETL, the EIL, and the cathode illustrated in FIG. 1. An organic EL device according to one embodiment may further include one or two intermediate layers if required. The HIL, the EIL, the HBL, and the like, are optional. However, the luminescence efficiency can be improved with these layers.

Hereinafter, examples of synthesizing the compound of formula (2), which is a representative organic luminescent compound with at least two phenylcarbazole derivatives in a side chain, and examples of manufacturing organic EL devices using the compound of formula (2) will be described. The following examples are for illustrative purposes and are not intended to limit the scope of the present embodiments. The phenylcarbazole compounds of formula (1) above are luminescent materials with superior luminescence and hole transport characteristics and can be used as a blue luminescent material and green and red phosphorescent and fluorescent host materials.

Synthesis Example 1

Synthesis of Intermediates for Compound 2

Compound 2 was synthesized through reaction pathways illustrated in reaction schemes (1) and (2) below.

Reaction Scheme (1)

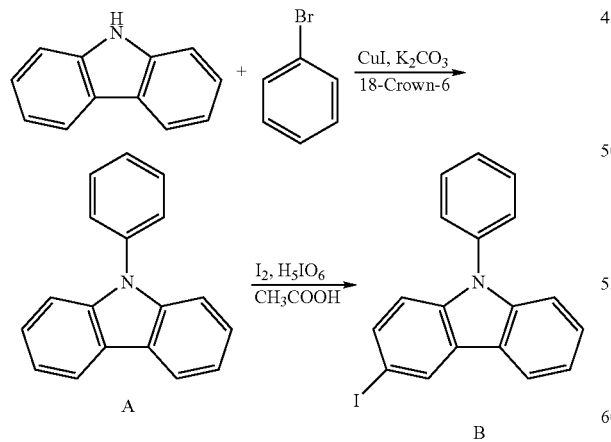

Synthesis of Intermediate A 3.344 g (20 mmol) of carbazole was added to 40 mL of 1,3-dimethyl-3,4,5,6-tetrahydro-s(1H)-pyrimidinone, and CuI 0.761 g (4 mmol) of CuI, 11.057 g (80 mmol) of $K_2CO_3$, and 0.1 g (4 mmol) of 18-Crown-6 were added to the mixture. The resultant mixture was stirred at 170° C. for 20 hours, cooled to room temperature, and distilled under reduced pressure to remove the solvent. 100 mL of dichloromethane was added to dissolve the residue and washed several times with water. The washed dichloromethane layer was dried using $MgSO_4$ and dried under reduced pressure to obtain a crude product. The crude product was purified using silica gel column chromatography and recrystallized using hexane to obtain 3.28 g of a solid intermediate A with a yield of 67%.

Synthesis of Intermediate B 2.433 g (10 mmol) of intermediate A was added to 100 mL of 80% acetic acid, and 1.357 g (5.35 mmol) of 12 and 0.333 g (1.46 mmol) of ortho-periodic acid ($H_5IO_6$) in solid state were added to the mixture. The resultant mixture was stirred at 80° C. in a nitrogen atmosphere for 2 hours. After the termination of reactions, an organic layer was extracted three times with 50 mL of ethyl ether each. The collected organic layer was dried by evaporating the solvent, and the residue was purified using silica gel column chromatography to obtain 3.23 g of intermediate B with a yield of 87%.

Reation scheme (2)

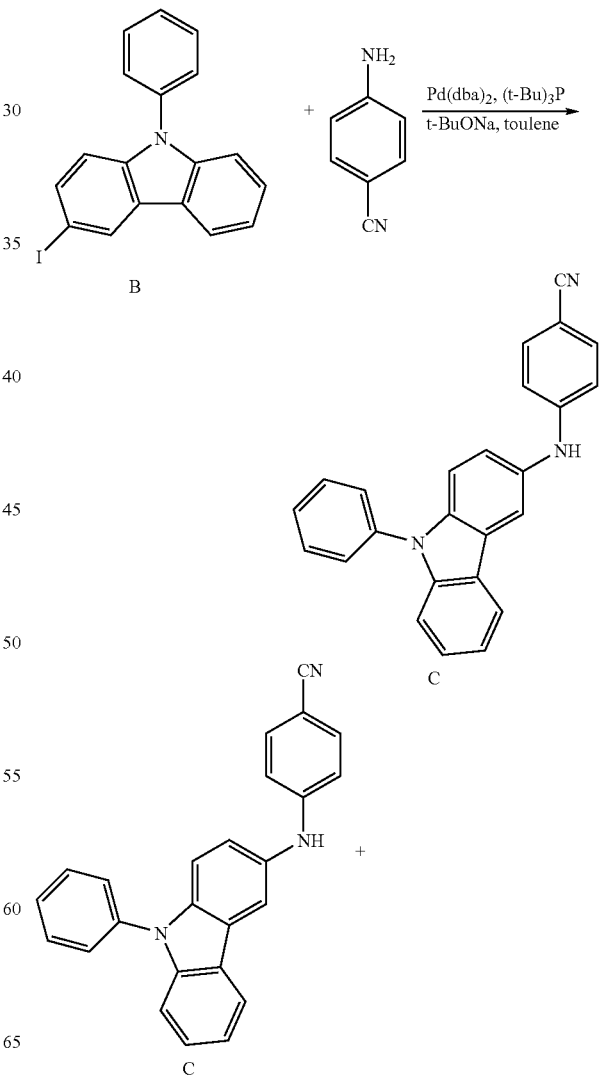

-continued

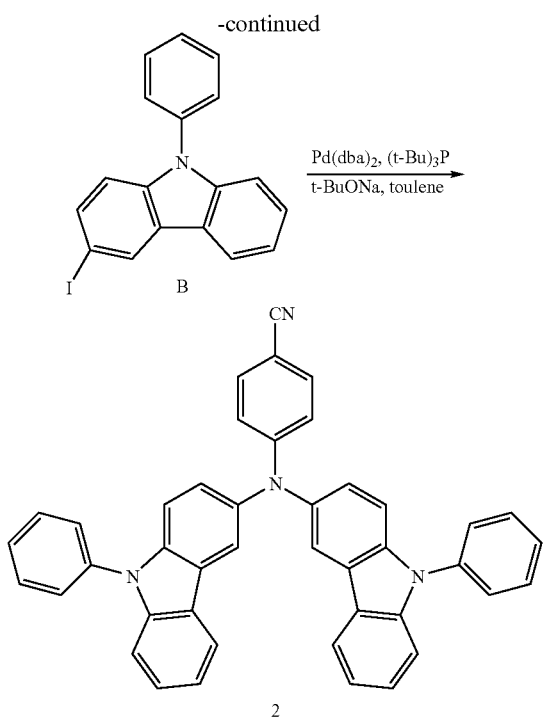

2

Synthesis of Intermediate C 0.316 g (0.856 mmol) of intermediate B and 0.142 g (1.2 mmol) of 4-aminobenzonitrile were dissolved in 5 mL of toluene. 0.144 g (1.5 mmol) of t-BuONa, 0.018 g (0.02 mmol) of Pd(dba)$_2$, and 0.004~0.006 g (0.02~0.03 mmol) of (t-Bu)$_3$P were added to the solution and stirred at 80° C. for 5 hours. An organic layer was extracted from the reaction solution three times with 20 mL of ethyl ether each. The collected organic layer was dried using MgSO$_4$, and the solvent was vaporized. The resulting residue was purified using silica gel column chromatography to obtain 0.218 g of intermediate C with a yield of 71%.

Synthesis Example 2

Synthesis of Compound 2

Compound 2, which is also represented by formula (5) in the detailed description and claims, was synthesized as follow.

0.221 g (0.614 mmol) of intermediate C and 0.332 g (0.9 mmol) of intermediate B were dissolved in 10 mL of toluene. 0.144 g (1.5 mmol) of t-BuONa, 0.018 g (0.02 mmol) of Pd(dba)$_2$, 0.004~0.006 g (0.02~0.03 mmol) of (t-Bu)$_3$P were added to the solution and stirred at 90° C. for 6 hours. An organic layer was extracted from the reaction solution three times with 30 mL of ethyl ether each. The collected organic layer was dried using MgSO$_4$, and the solvent was vaporized. The resulting residue was purified using silica gel column chromatography to obtain 0.236 g of Compound 2 with a yield of 64%. The structure of Compound 2 was identified by $^1$H-NMR: $^1$H-NMR (CDCl$_3$, 400 MHz) δ (ppm) 8.05 (d, 2H), 8.03 (dd, 2H), 7.58 (m, 8H), 7.47 (m, 2H), 7.39 (m, 8H), 7.33 (dd, 2H), 7.24 (m, 2H), 6.94 (d, 2H).

EXAMPLE 1

An indium tin oxide (ITO) substrate (available from Corning Co. (New York, N.Y.)) having a resistance of 15 Ω/cm$^2$ (1200 Å) was cut to a size of 50 mm×50 mm×0.7 mm and washed in isopropyl alcohol and pure water for 5 minutes each by ultrasonication and UV irradiation and using ozone. The washed substrate was loaded into a vacuum deposition apparatus. Initially, a hole injecting layer was formed of IDE 406 on the substrate to a thickness of 600 Å by vacuum deposition. Next, a hole transporting layer was formed on the hole injecting layer by depositing 4,4'-bis[N-(1-naphthyl)-N-phenylamino]biphenyl (NPB) in a vacuum to a thickness of 300 Å. After the formation of the hole transporting layer, an emitting layer was formed by simultaneously depositing on the hole transporting layer Compound 2 as a phosphorescent host and Ir(ppy)$_3$ as a green phosphorescent dopant in a ratio of 93:7 to a thickness of 300 Å. A hole blocking layer was formed on the emitting layer by depositing Balq to a thickness of 50 Å. An electron transporting layer was formed on the hole blocking layer by depositing Alq$_3$ to a thickness of 300 Å. Finally, a LiF/Al electrode (EIL/cathode) was formed on the electron transporting layer by sequentially depositing alkali metal halide, LiF, to a thickness of 10 Å and Al to a thickness of 3000 Å in a vacuum to obtain a complete organic EL device as illustrated in FIG. 1.

This organic EL device had a current density of 20.09 mA/cm$^2$ at 6V DC, a luminance of 1,075 cd/m$^2$, which is high, a chromaticity coordinate (0.30, 0.60), and a luminescence efficiency of 5.35 cd/A.

EXAMPLE 2

An organic EL device was manufactured in the same manner as in Example 1, except that Compound 2 of Example 2 (Formula 5) as a phosphorescent host and RD61 (available from Universal Display Corporation, Ewing, N.J.) as a red phosphorescent dopant were simultaneously deposited on the hole transporting layer in a ratio of 90:10 by weight.

This organic EL device had a current density of 30.00 mA/cm$^2$, at 6V DC, a luminance of 2,011 cd/m$^2$, which is high, a chromaticity coordinate (0.62, 0.38), and a luminescence efficiency of 6.70 cd/A.

EXAMPLE 3

An organic EL device was manufactured in the same manner as in Example 1, except that Compound 2 as a phosphorescent host and SDI BD 235M (Tris-(2,6-difluoro-3-(4-methylpyridin-2-yl)benzonitril-4,N-yl Ir)) as a blue phosphorescent dopant were simultaneously deposited on the hole transporting layer in a ratio of 93:7 by weight.

Figure 6:
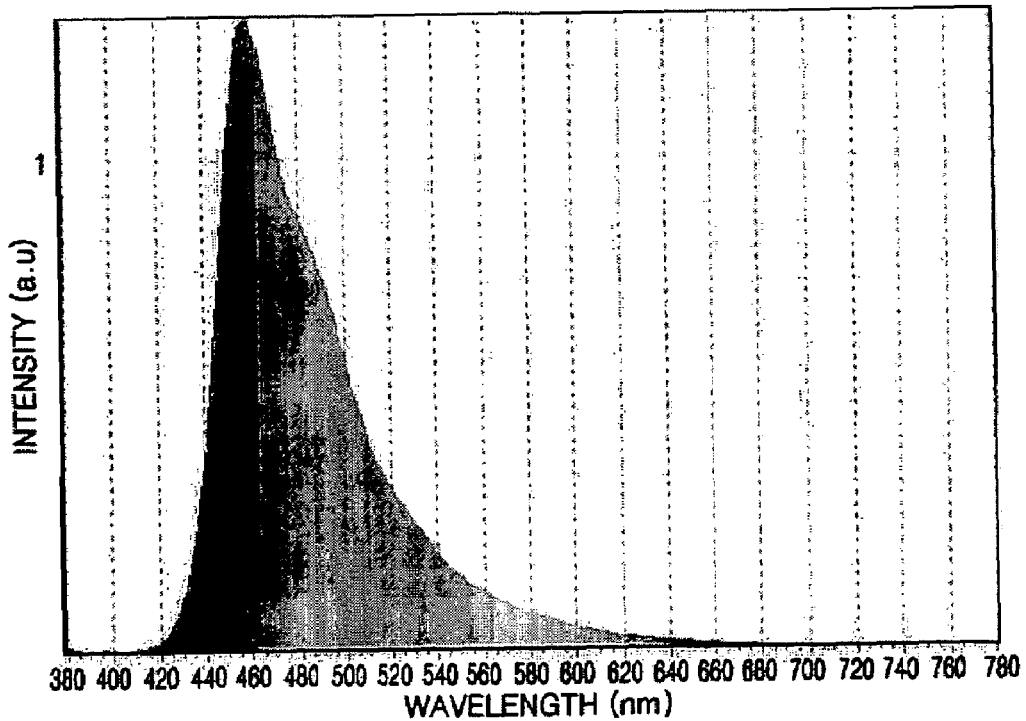
FIG. 6 is a spectrum illustrating strong absorbance of a compound according to one embodiment in the blue region.

This organic EL device had a current density of 32.32 mA/cm$^2$ at 6V DC, a luminance of 400 cd/m$^2$, and a chromaticity coordinate (0.16, 0.18), which lies in a blue range as illustrated in FIG. 6.

Comparative Example 1

An organic EL device was manufactured in the same manner as in Example 1, except that CBP (4,4'-N,N'-dicarbazolebiphenyl) which is a common phosphorescent host, instead of Compound 2 and Ir(ppy)$_3$ as a green phosphorescent dopant were simultaneously deposited in a ratio of 93:7 by weight to form the organic emitting layer. This organic EL device had a current density of 4.30 mA/cm$^2$ at 6V DC, a luminance of 965.2 cd/m$^2$, and a chromaticity coordinate (0.30, 0.60), which was the same as in Example 1.

Figure 2:
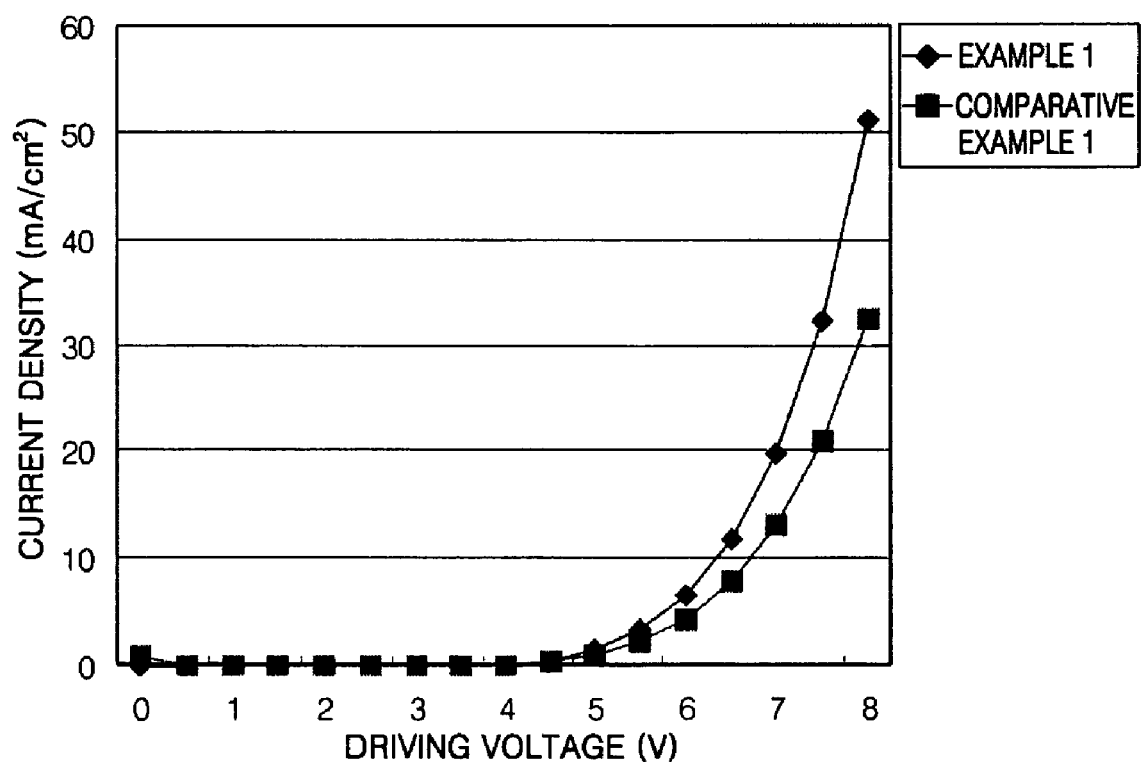
FIG. 2 is a graph of current density versus driving voltage for an organic EL device manufactured in Example 1 using a compound according to one of the present embodiments as a host and a green dopant and an organic EL device manufactured in Comparative Example 1.
Figure 3:
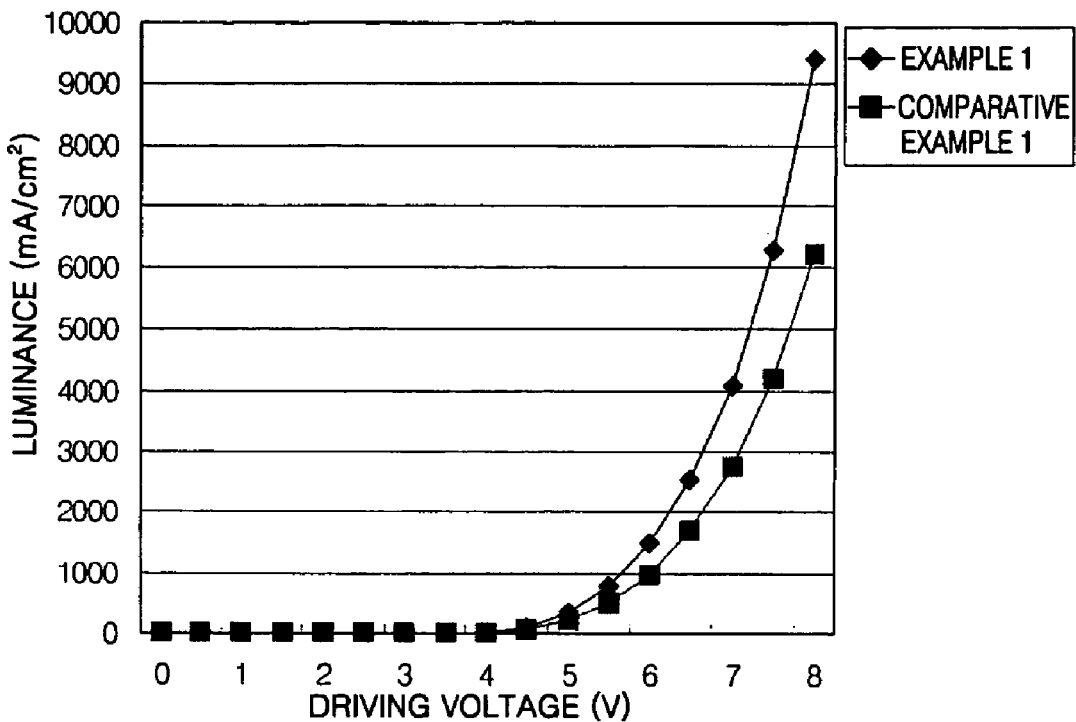
FIG. 3 is a graph of luminance versus driving voltage for the organic EL device manufactured in Example 1 according to the present embodiments and the organic EL device manufactured in Comparative Example 1.

In the organic EL device manufactured using Compound 2 according to one embodiment as a green phosphorescent host in Example 1, the ability to transport charges was greatly improved, and a turn-on voltage dropped to 1V, compared with the organic EL device of Comparative Example 1. In addition, in the organic EL device of Example 1, the current density is considerably greater than in the organic EL device of Comparative Example 1 at a given driving voltage, and thus the luminance is also greater than in the organic EL device of Comparative Example 1. The current density and luminance data of the organic EL devices manufactured in Example 1 and Comparative Example 1 are comparatively shown in FIGS. 2 and 3.

Comparative Example 2

An organic EL device was manufactured in the same manner as in Example 2, except that CBP, which is a common phosphorescent host, instead of Compound 2 and RD 61 as a red phosphorescent dopant were simultaneously deposited in a ratio of 90:10 by weight to form the organic emitting layer. This organic EL device had a current density of a current density of 13.53 mA/cm² at 6V DC, a luminance of 1,299 cd/m², a chromaticity coordinate (0.62, 0.38), which was the same as in Example 2, and a luminescence efficiency of 6.70 cd/A.

Figure 4:
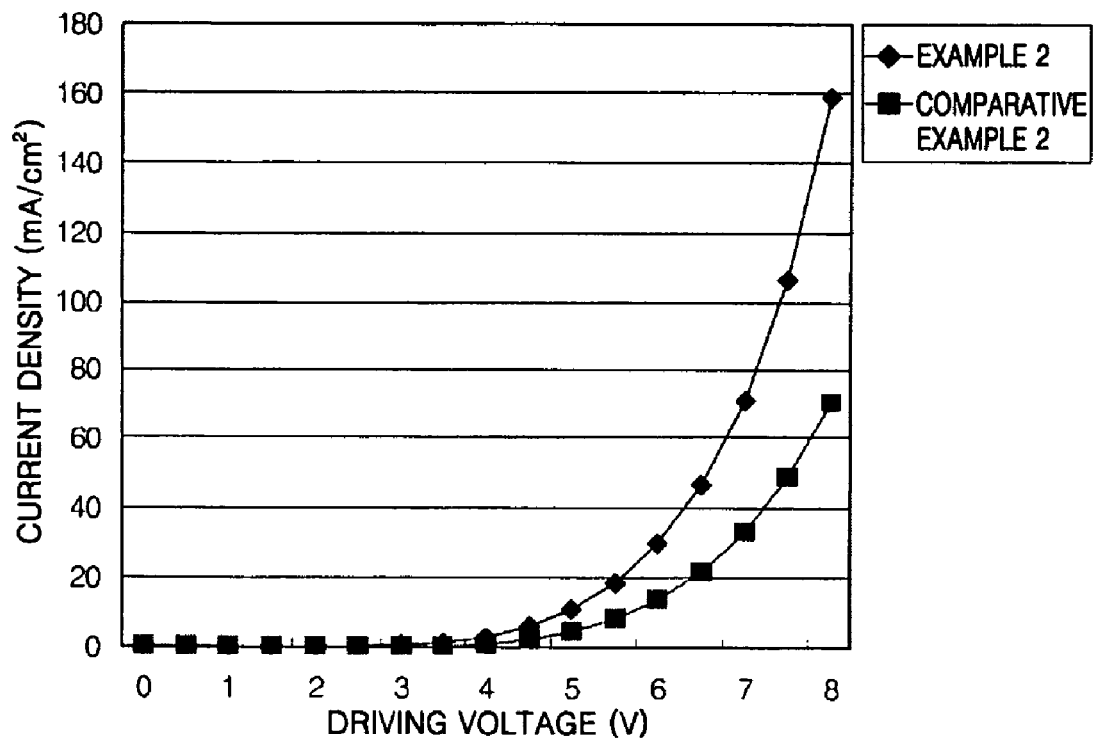
FIG. 4 is a graph of luminance versus driving voltage for an organic EL device manufactured in Example 2 using the compound according to the present embodiment as a host and a red dopant and an organic EL device manufactured in Comparative Example 2.
Figure 5:
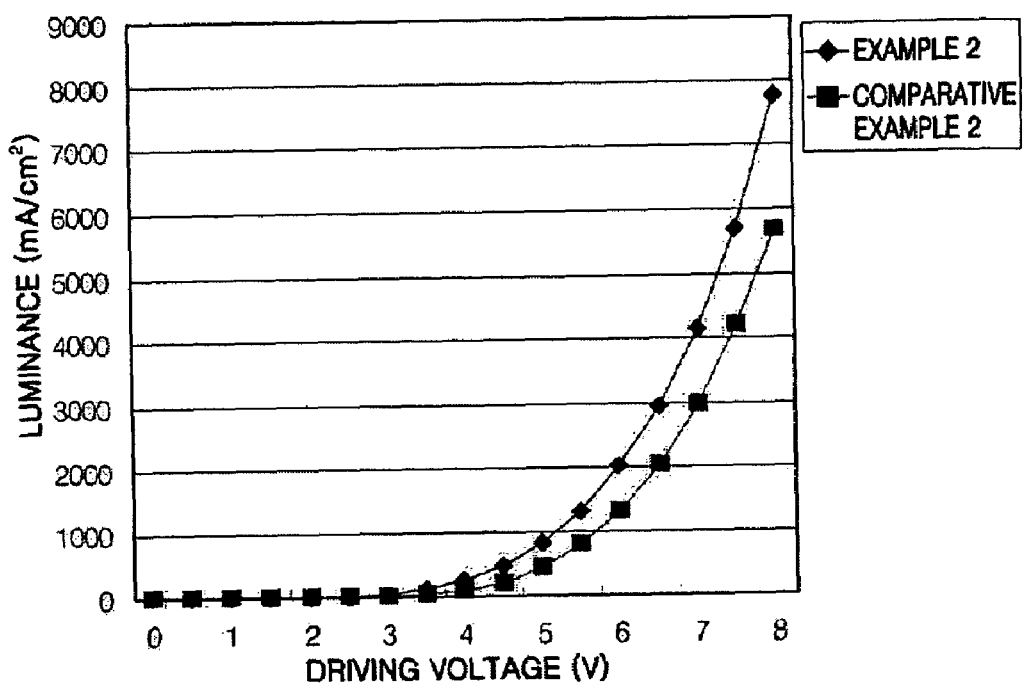
FIG. 5 is a graph of current density versus driving voltage for the organic EL device manufactured in Example 2 according to the present embodiment and the organic EL device manufactured in Comparative Example 2.

In the organic EL device manufactured using Compound 2 according to one embodiment as a red phosphorescent host in Example 2, the ability to transport charges was greatly improved, and a turn-on voltage dropped to 0.5V, compared with the organic EL device of Comparative Example 1. In addition, in the organic EL device of Example 2, the current density is considerably greater than in the organic EL device of Comparative Example 2 at a given driving voltage, and thus the luminance is also greater than in the organic EL device of Comparative Example 2. The current density and luminance data of the organic EL devices manufactured in Example 2 and Comparative Example 2 are comparatively shown in FIGS. 4 and 5.

TABLE 1

|  | Current density (mA/cm²) | Luminance (cd/m²) | Chromaticity coordinate |
| --- | --- | --- | --- |
| Example 1 | 20.09 | 1,075 | (0.30, 0.60) |
| Example 2 | 30.00 | 2,011 | (0.62, 0.38) |
| Example 3 | 32.32 | 400 | (0.18, 0.16) |
| Comparative Example 1 | 4.30 | 965.2 | (0.30, 0.60) |
| Comparative Example 2 | 13.53 | 1,299 | (0.62, 0.38) |

As described above, organic luminescent compounds according to the current embodiments, such as compounds of formulae (1), (3), (4) and (5) above, that include at least two phenylcarbazole derivatives in a side chain have superior electrical characteristics and charge transporting ability and thus can be used as host materials suitable for fluorescent and phosphorescent dopants of red, green, blue, white, and other colors and as charge transporting materials. A high efficiency, low voltage, high luminance, long lifespan organic EL device can be manufactured using the organic luminescent compounds.

While the present embodiments have been particularly shown and described with reference to exemplary embodiments thereof, it will be understood by those of ordinary skill in the art that various changes in form and details may be made therein without departing from the spirit and scope of the present embodiment as defined by the following claims.

What is claimed is:

1. A phenylcarbazole compound of formula (1) below:

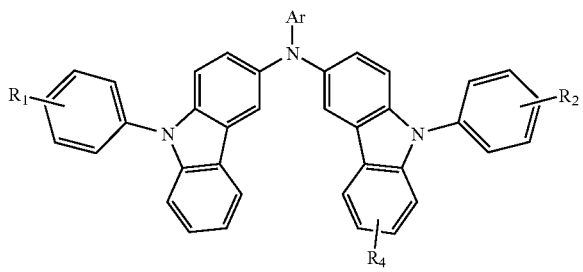

(1)

wherein each of $R_1$ and $R_2$ is independently a hydrogen atom or a monosubstituted or polysubstituted functional group selected from the group consisting of a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$ and $R_2$ can bind and form a saturated or unsaturated cyclic hydrocarbon group, Ar is a phenyl group, a lower alkylphenyl group, a lower alkoxyphenyl group, a phenoxyphenyl group, a halophenyl group, a cyanophenyl group, a dicyanophenyl group, a (α,α-dimethylbenzene)phenyl group, a (N,N'-dimethyl)aminophenyl group, a (N,N'- diphenyl) aminophenyl group, a pentalenyl group, a indenyl group, a naphthyl group, a lower alkylnaphthyl group, a lower alkoxynaphthyl group a cyanonaphthyl group, a halonaphthyl group, an anthracenyl group, an azulenyl group, a heptalenyl group, an acenaphthylenyl group, a fluorenyl group, an anthraquinoyl group, a methylanthryl group, a phenanthryl group, a triphenylene group, a pyrenyl group, a chrysenyl group, an ethyl chrysenyl group, a picenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a phenanthrenyl group, a ovalenyl group, carbazoyl, lower alkyl carbazoly, biphenyl, lower alkylbiphenyl, lower alkoxybiphenyl, thiophenyl, indoyl or pyrridyl group, and $R_4$ is a hydrogen atom or has formula (2) below,

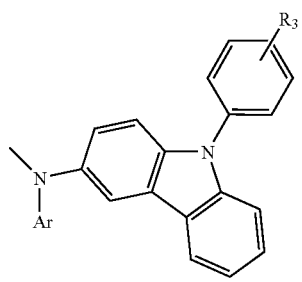

(2)

where $R_3$ is a monosubstituted or polysubstituted functional group selected from the group consisting of a hydrogen atom, a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, and a substituted or unsubstituted $C_6$-$C_{30}$ condensed polycyclic group; and Ar is a substituted or unsubstituted $C_6$-$C_{30}$ aryl group or a $C_6$-$C_{30}$ heteroaryl group.

2. The phenylcarbazole compound of claim 1 having the formula (3) below:

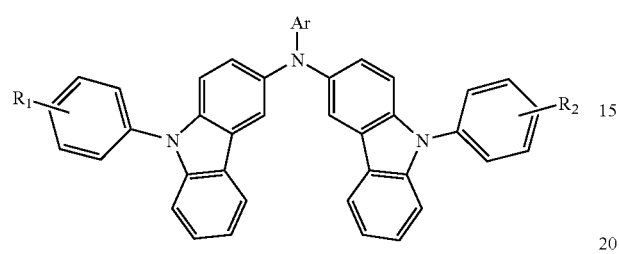

(3)

wherein each of $R_1$, and $R_2$, is independently a hydrogen atom or a monosubstituted or polysubstituted functional group selected from the group consisting of a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$, $R_2$, and $R_3$ can bind and form a saturated or unsaturated cyclic hydrocarbon group.

3. The phenylcarbazole compound of claim 1 having the formula (4) below:

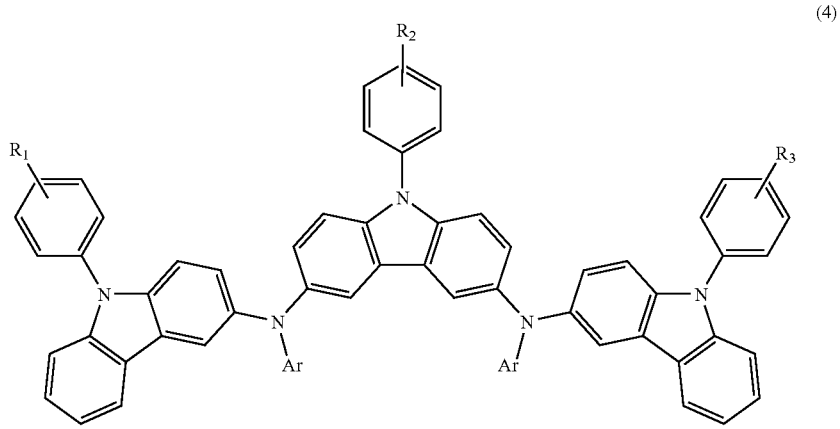

(4)

wherein each of $R_1$, $R_2$, and $R_3$ is independently a hydrogen atom or a monosubstituted or polysubstituted functional group selected from the group consisting of a substituted or unsubstituted $C_1$-$C_{30}$ alkyl group, a substituted or unsubstituted $C_6$-$C_{30}$ aryl group, a substituted or unsubstituted $C_4$-$C_{30}$ heterocyclic group, a substituted or unsubstituted $C_6$-$C_{30}$ condensed polycyclic group, wherein groups adjacent to $R_1$, $R_2$, and $R_3$ can bind and form a saturated or unsaturated cyclic hydrocarbon group.

4. The phenylcarbazole compound of claim 1, having the structure of formula (5) below:

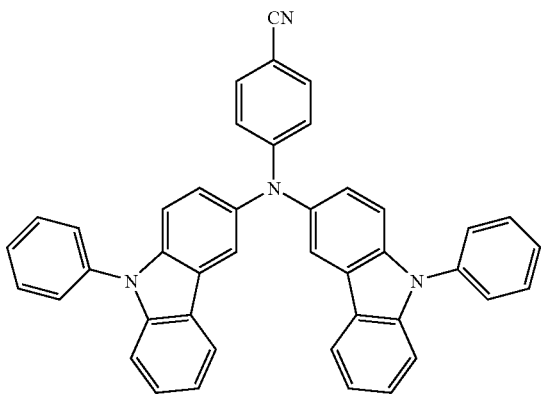

(5)

5. The phenylcarbazole compound of claim 1, wherein each of $R_1$, $R_2$, and $R_3$ may be a substituted or unsubstituted $C_6$-$C_{30}$ aryl group independently selected from the group consisting of a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazoyl group, a lower alkyl carbazoyl group, a biphenyl group, a lower alkylbiphenyl group, a lower alkoxybiphenyl group, a thiophenyl group, an indoyl group, a pyridyl group, and a phenanthrenyl group.

6. The phenylcarbazole compound of claim 5, wherein the Ar can be selected from the group consisting of a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazoyl group, a lower alkyl carbazoyl group, a biphenyl group, a lower alkylbiphenyl group, a lower alkoxybiphenyl group, a thiophenyl group, an indoyl group, a pyrridyl group, and a phenanthrenyl group.

7. The phenylcarbazole compound of claim 1, wherein Ar may be selected from the group consisting of a fluorenyl group, a carbazoyl group, a phenyl group, a naphthyl group, and a phenanthrenyl group.

8. The phenylcarbazole compound of claim 1, wherein the compound is

1
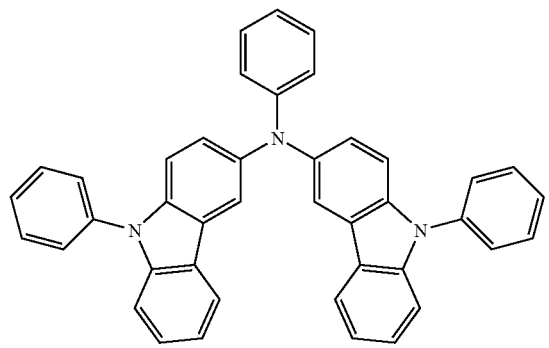

2
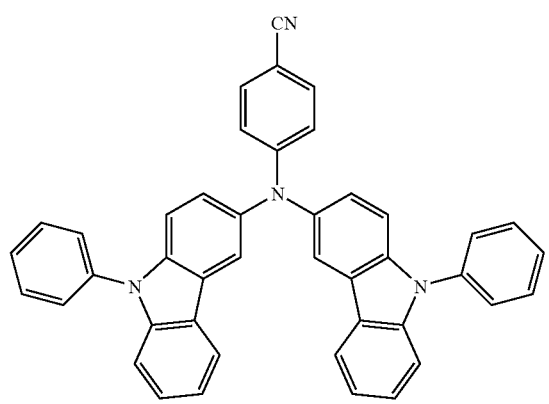

3
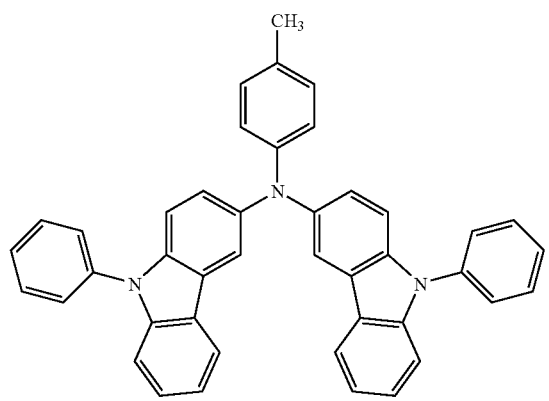

-continued

4
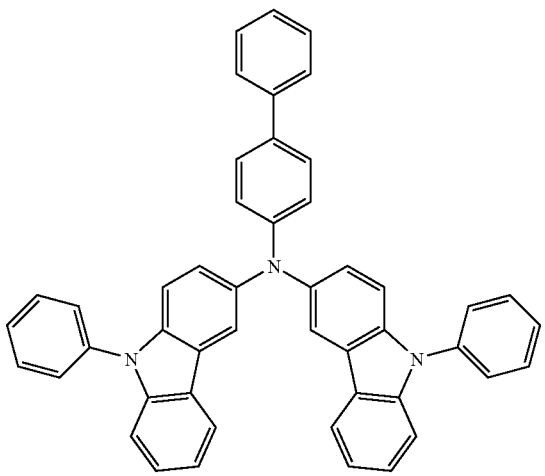

5
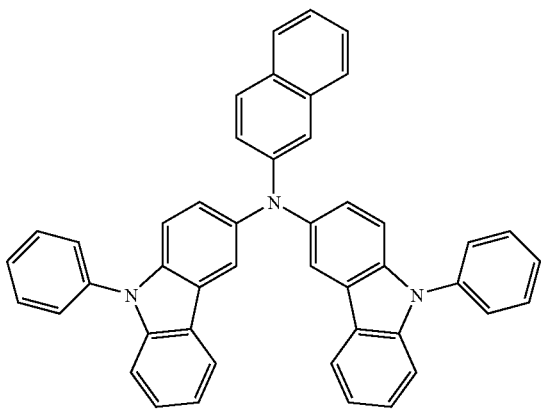

6
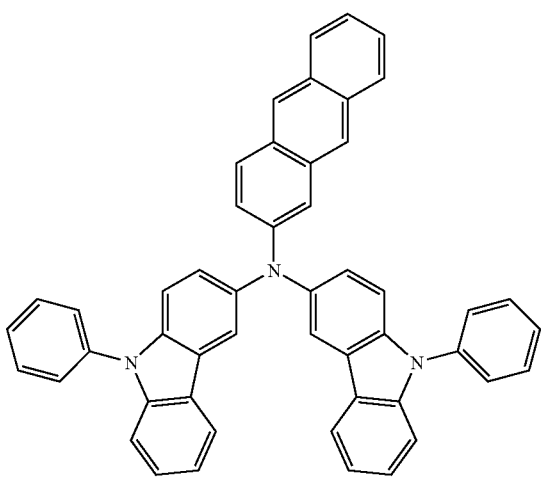

7
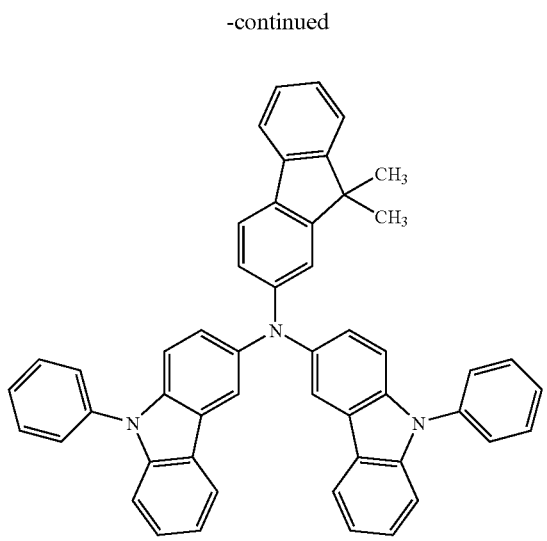
8
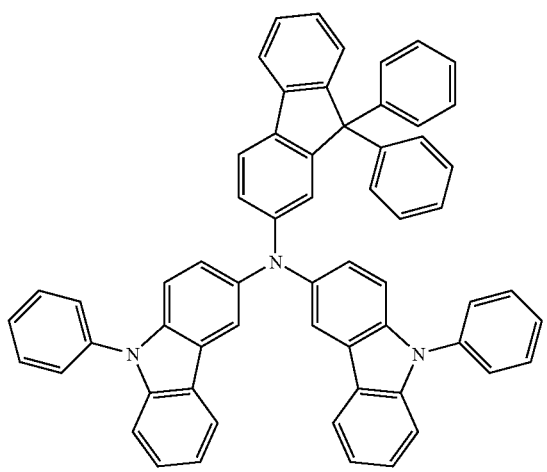
9
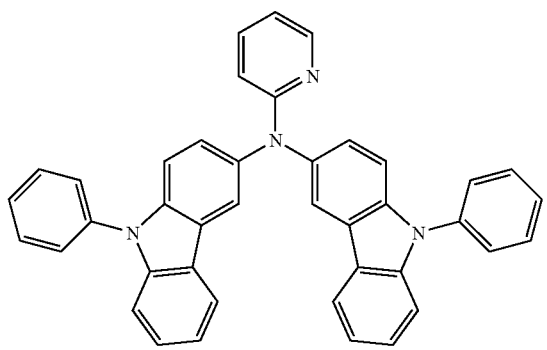
10
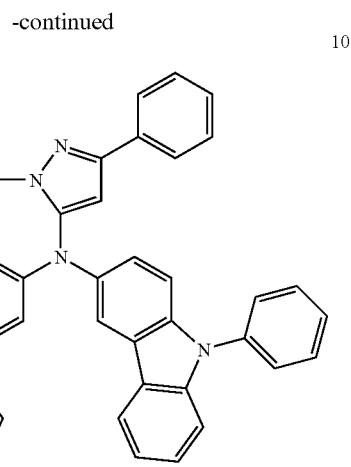
11
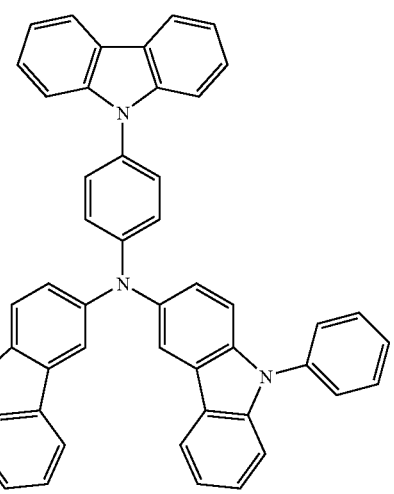
12

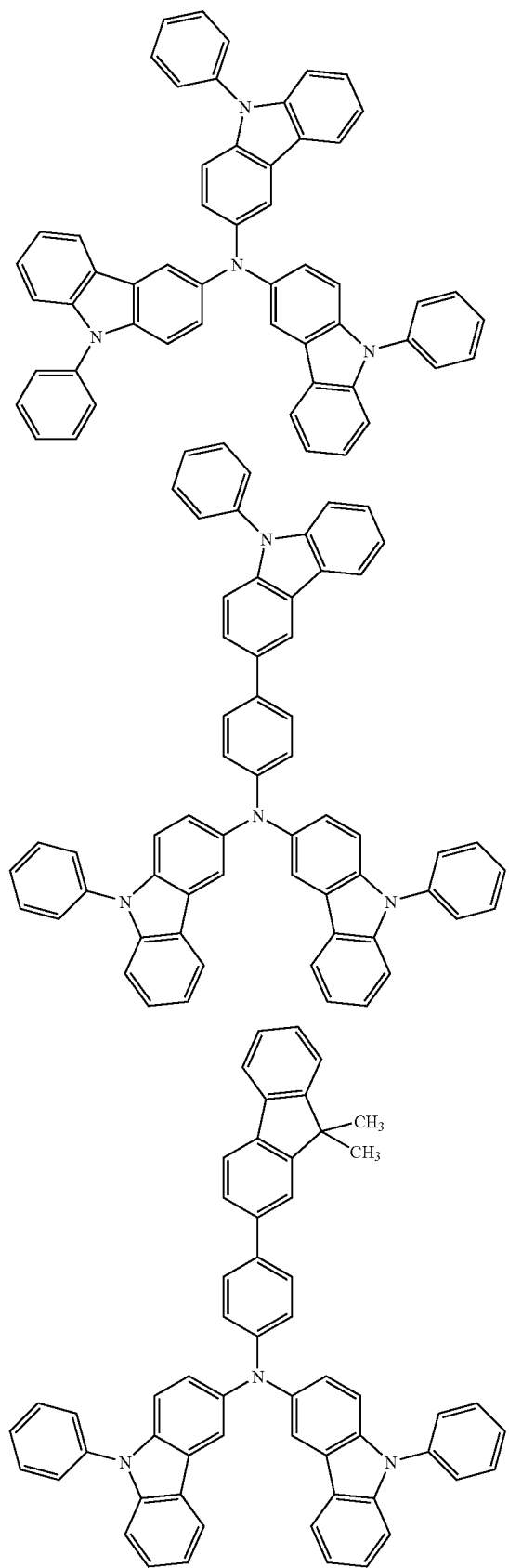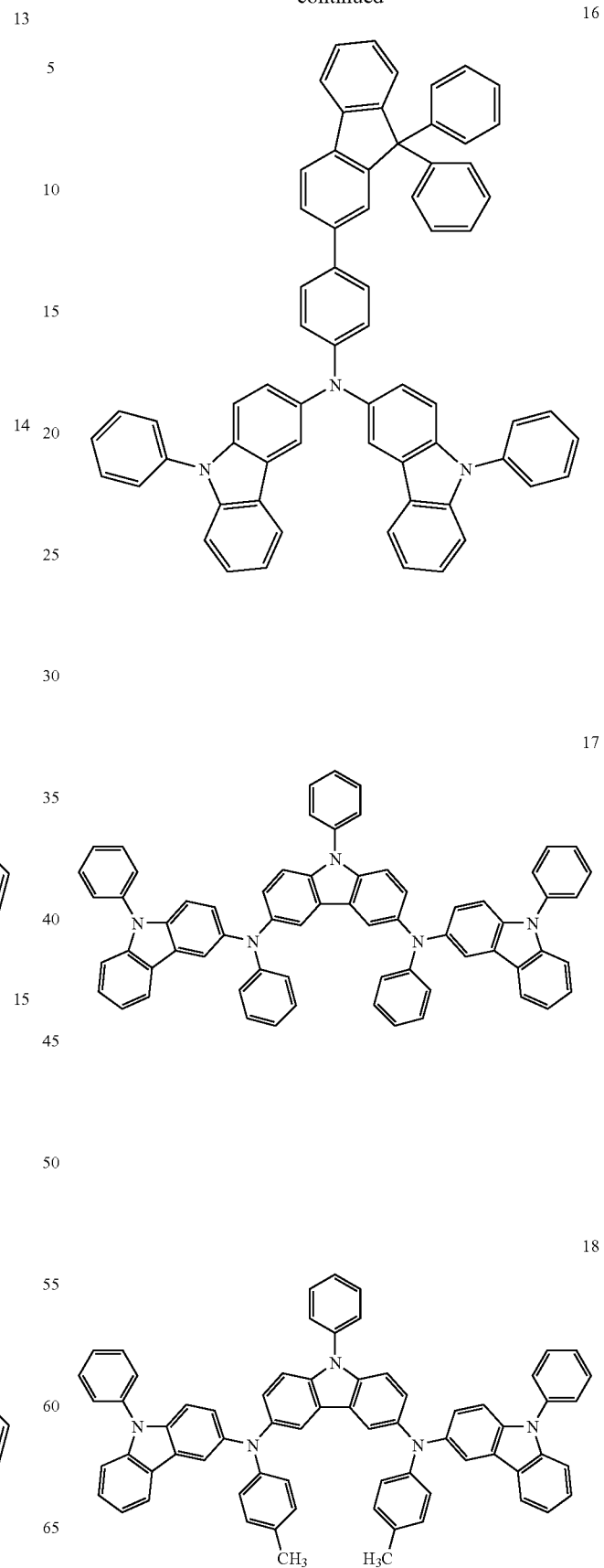

-continued

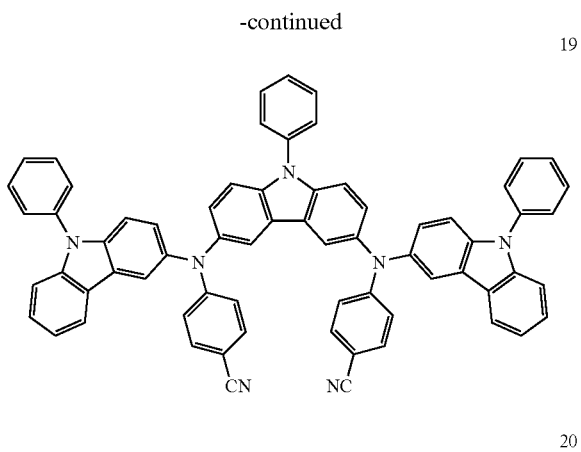
19

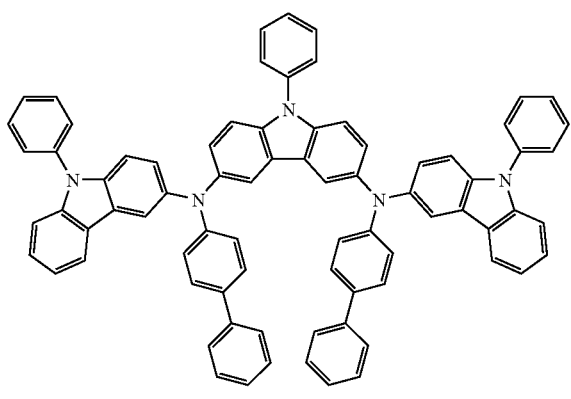
20

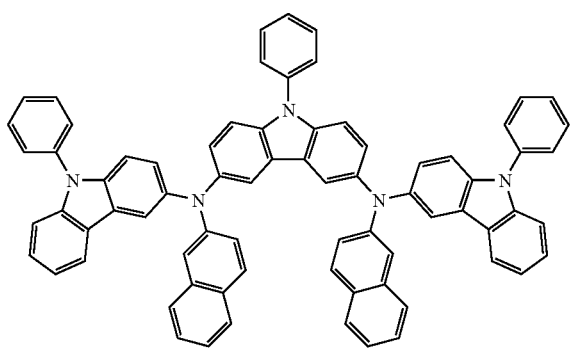
21

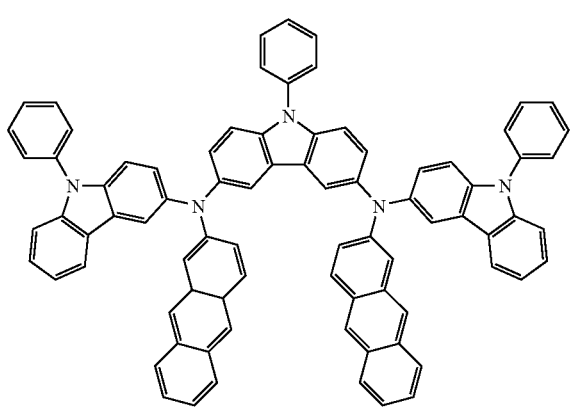
22

-continued

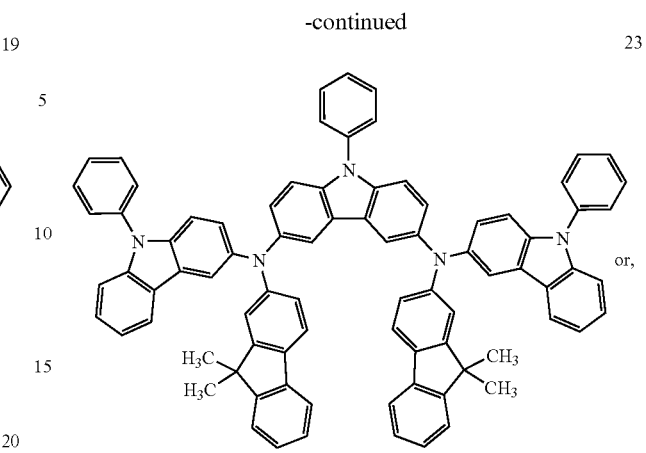
23

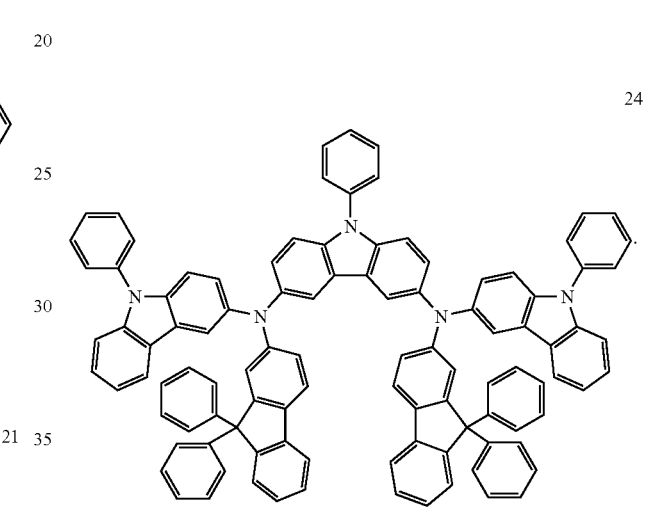
24 or,

9. An organic electroluminescence device comprising:
a pair of electrodes; and
an organic layer containing the phenylcarbazole compound according to claim 1.

10. An organic electroluminescence device comprising:
a pair of electrodes; and
an organic layer containing the phenylcarbazole compound according to claim 2.

11. An organic electroluminescence device comprising:
a pair of electrodes; and
an organic layer containing the phenylcarbazole compound according to claim 3.

12. An organic electroluminescence device comprising:
a pair of electrodes; and
an organic layer containing the phenylcarbazole compound according to claim 4.

13. An organic electroluminescence device comprising:
a pair of electrodes; and
an organic layer containing the phenylcarbazole compound according to claim 5.

14. An organic electroluminescence device comprising:
a pair of electrodes; and
an organic layer containing the phenylcarbazole compound according to claim 6.

15. An organic electroluminescence device comprising:
a pair of electrodes; and
an organic layer containing the phenylcarbazole compound according to claim 7.

16. The organic electroluminescence device of claim 9, wherein the organic layer is an emitting layer.

17. The organic electroluminescence device of claim 9, wherein the organic layer further includes at least one selected from among a hole injecting layer, a hole transporting layer, an electron injecting layer, an electron transporting layer, and a hole blocking layer.

18. The organic electroluminescence device of claim 9, wherein the organic layer is a hole injecting layer or a hole transporting layer.

19. The organic electroluminescence device of claim 9, wherein the emitting layer contains blue, green, and red dopants.

20. The organic electroluminescence device of claim 12, wherein the amount of the blue, green, and red dopants in the emitting layer is in a range of about 0.1 to about 10 parts by weight based on 100 parts by weight of the phenylcarbazole compound.

* * * * *

UNITED STATES PATENT AND TRADEMARK OFFICE
CERTIFICATE OF CORRECTION

PATENT NO. : 7,431,997 B2
APPLICATION NO. : 11/181706
DATED : October 7, 2008
INVENTOR(S) : Hwang et al.

It is certified that error appears in the above-identified patent and that said Letters Patent is hereby corrected as shown below:

Column 3 (Structure 3), Line 1, delete " 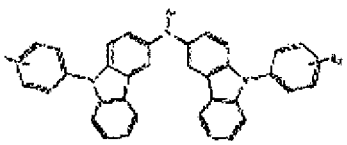 " and replace it with -- 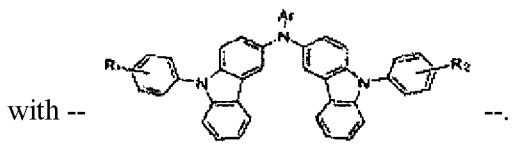 --.

Column 4, Line 34, delete "group," and replace it with -- group. --.

Column 6, Line 2, delete "$C_6$-$c_{30}$" and replace it with -- $C_6$-$C_{30}$ --.

Column 6, Line 57, delete "carbazoly," and replace it with -- carbazolyl, --.

Column 7, Line 54, delete "napthyl," and replace it with -- naphthyl, --.

Column 7, Line 56, delete "napthylenyl," and replace it with -- naphthylenyl, --.

Column 7, Line 56, delete "heptaleny;" and replace it with -- heptalenyl; --.

Column 8, Line 27, delete "structos" and replace it with -- structures --.

Column 20, Line 16, delete "12" and replace it with -- $I_2$ --.

Column 20, Line 31, delete "toulene" and replace it with -- toluene --.

Column 21, Line 8, delete "toulene" and replace it with -- toluene --.

Claim 1, Column 24, Line 34, delete "group" and replace it with -- group, --.

Claim 1, Column 24, Lines 45-46, delete "carbazoly," and replace it with -- carbazolyl, --.

UNITED STATES PATENT AND TRADEMARK OFFICE
CERTIFICATE OF CORRECTION

PATENT NO.        : 7,431,997 B2
APPLICATION NO.   : 11/181706
DATED             : October 7, 2008
INVENTOR(S)       : Hwang et al.

It is certified that error appears in the above-identified patent and that said Letters Patent is hereby corrected as shown below:

Claim 2, Column 25, Line 23, delete "$R_l$," and replace it with -- $R_1$ --.

Signed and Sealed this

Second Day of June, 2009

JOHN DOLL
*Acting Director of the United States Patent and Trademark Office*